United States Patent
Levy et al.

(10) Patent No.: US 6,887,880 B2
(45) Date of Patent: May 3, 2005

(54) ADENINE BASED INHIBITORS OF ADENYLYL CYCLASE, PHARMACEUTICAL COMPOSITIONS, AND METHOD OF USE THEREOF

(75) Inventors: Daniel Levy, San Carlos, CA (US); Charles Marlowe, Redwood City, CA (US); Kim Kane-Maguire, Belmont, CA (US); Robert M. Scarborough, Half Moon Bay, CA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 09/989,348

(22) Filed: Nov. 20, 2001

(65) Prior Publication Data

US 2002/0068745 A1 Jun. 6, 2002

Related U.S. Application Data

(60) Provisional application No. 60/249,465, filed on Nov. 20, 2000.

(51) Int. Cl.$^7$ ...................... C07D 473/34; A61K 31/52; A61P 9/04
(52) U.S. Cl. .............. 514/263.2; 514/263.22; 514/263.23; 514/263.4; 544/277
(58) Field of Search ........................ 544/277; 514/263.2, 514/263.22, 263.23, 263.4

(56) References Cited

FOREIGN PATENT DOCUMENTS

| JP | 47030696 | * | 3/1971 | |
| WO | WO 9915509 A2 | * | 4/1999 | ......... C07D/239/54 |

OTHER PUBLICATIONS

Maurinsh, Y.; et al J. Org. Chem. 1997; 62(9); 2861–2871.*
Wolfrom, J. Organic Chem. 1099–1101 (1965).*
Okumura, J. Medical Chem, 17(8), 846 (1974) pp. 846–855.*
Saito, Tet. Letters (1970) 4863–4866.*
Holy, Coll. Czech. Chem. Comm. 50, 262 (1885).*

* cited by examiner

Primary Examiner—Mark L. Berch
(74) Attorney, Agent, or Firm—Townsend and Townsend and Crew LLP

(57) ABSTRACT

The present invention relates to derivatives and analogues of adenine of the formula:

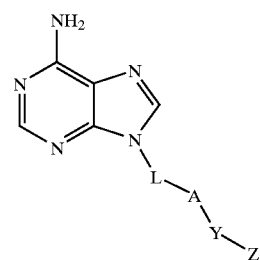

wherein L, A, Y and Z are those defined herein. Compounds of the present invention are useful in inhibiting adenylyl cyclase activity. The present invention also relates to a method of preventing and inhibiting a patient's fibroproliferative vasculopathy following vascular injury or a vascular surgical operation which includes administering to the patient, an effective amount of a compound according to the invention subsequent to a vascular injury, or subsequent to a vascular surgical operation, for one to two weeks after the injury or surgical operation, effective to treat or prevent a patient's fibroproliferative vasculopathy such as chronic allograft rejection or vascular restenosis following vascular trauma. The present invention also relates to a method for measuring the inhibition of adenylyl cyclase activity and a method for treating congestive heart failure.

15 Claims, No Drawings

ADENINE BASED INHIBITORS OF ADENYLYL CYCLASE, PHARMACEUTICAL COMPOSITIONS, AND METHOD OF USE THEREOF

RELATED APPLICATION

This application claims the benefit of priority under 35 U.S.C. §119(e) to U.S. Provisional Application Ser. No. 60/249,465 filed on Nov. 20, 2000, which is herein incorporated in its entirety by reference.

FIELD OF INVENTION

The present invention relates to derivatives and analogues of adenine, which inhibit adenylyl cyclase activity, and are thus useful to treat congestive heart failure. Additionally, the compounds of the present invention are useful to inhibit or prevent a patient's fibroproliferative vasculopathy following vascular injury or a vascular surgical operation. The method according to the invention includes administering to the patient an effective amount of a compound according to the inventions subsequent to the diagnosis of congestive heart failure, the occurrence of a vascular injury, or subsequent to a vascular surgical operation. Administration of the compounds of the present invention is continued either chronically after diagnosis of congestive heart failure or for one to two weeks after the injury or surgical operation. The amount of compound administered is the amount determined effective to treat congestive heart failure or to prevent a patient's fibroproliferative vasculopathy such as chronic allograft rejection or vascular restenosis following vascular trauma. The present invention also relates to a method for measuring the inhibition of adenylyl cyclase activity.

BACKGROUND ART

Adenylyl cyclases are a family of enzymes that catalyze the formation of cAMP from adenosine-5'-triphosphate (5'ATP), mediate the physiological effects of numerous hormones and neurotransmitters, and belong to a super family of membrane-bound transporters and channel proteins.

Adenosine-3':5'-cyclic monophosphate (cAMP) is known to be the second messenger involved in signal transduction for numerous neurotransmitters and hormones, and thus has an impact upon some of the key mediators for SMC proliferation and migration. While it is known that the cAMP pathway can be regulated pharmacologically by inhibitory compounds that are of particular value in the treatment of many diseases, and there is still much interest in identifying more potent and specific agents acting on this pathway. Regulation of this pathway can be achieved through changes in the activities of cAMP-phosphodiesterases, cAMP-dependent protein kinases, or adenylyl cyclases.

Inhibitory compounds have been developed as therapeutic agents that inhibit cyclic nucleotide phosphodiesterases. Some effects of such agents are to raise cellular cAMP levels in tissues and organs on which they act. For example, theophylline, an inhibitor of all isozyme families of phosphodiesterases, is used clinically to treat asthma. Rolipram, an inhibitor of type IV phosphodiesterase, is used in the treatment of depression. And several inhibitors of type III phosphodiesterase have been used clinically to treat patients with moderate to severe heart failure. These latter drugs enhance cardiac index without elevating mean arterial blood pressure and lowering systemic vascular resistance. Therefore such compounds are believed to have significant advantages over .beta.-agonists and digitalis.

However, there is a continued need for discovering more effective and specific inhibitory compounds that act directly on adenylyl cyclases, even though inhibitory agents which indirectly activate or indirectly inhibit the enzyme may be commonly used in the treatment of such diseases. For example, drugs of the class beta-blockers are commonly used to treat hypertension and some of these act to inhibit adenylyl cyclase indirectly by blocking the stimulatory effects of the sympathetic nervous system to activate adenylyl cyclase in the heart, thereby reducing cardiac output. Agents that reduce adenylyl cyclase activity directly would be expected to have a similar cardiac-sparing effect, along with reduced cardiomyopathy and heart failure. Adenylyl cyclases can be potently and directly inhibited by analogues of adenosine, via a specific domain. This binding domain is referred to as the "P"-site from an evident requirement for an intact purine moiety. However, there is a need for more potent and direct adenylyl cyclase inhibitors.

Congestive heart failure (CHF) afflicts 3 to 4 million Americans and 400,500 to 500,000 new cases are diagnosed each year, and adenylyl cyclase plays a role in the disease progression, as discussed below. Significantly, statistics show that more than 50% of heart failure (CHF) patients die within five years of their diagnosis. It is believed to be the primary cause of 30,000 to 40,000 deaths annually.

CHF is defined as an abnormal heart function resulting in an inadequate cardiac output for metabolic needs. See E. Braunwald, Heart Disease, First Ed., W. B. Saunders, Philadelphia, page 426 (1988). The symptoms of CHF include for example, breathlessness, fatigue, weakness, leg swelling, and exercise intolerance. Initially, the conditions of patients with heart failure usually develop as the heart muscle weakens and needs to work harder to keep the blood flowing through the body. The heart failure develops, following an injury to the heart as damage caused by heart attack, long term high blood pressure or an abnormality of one of the heart valves. The weakened heart must then work harder to keep the demands of the body. Heart failure is usually not recognized until a more advanced stage of heart failure which is referred to as congestive heart failure. On physical examination, patients with CHF tend to have elevations in heart and respiratory rates, rates (an indication of fluid in the lungs), edema, jugular venous distension, and, in general, enlarged hearts. The most common cause of CHF is atherosclerosis which causes blockages in the blood vessels (coronary arteries) that provide blood flow to the heart muscle. Ultimately, such blockages may cause myocardial infarction (death of heart muscle) with subsequent decline in heart function and resultant heart failure. Other causes of CHF include valvular heart disease, hypertension, viral infections of the heart, alcohol, and diabetes. Some cases of heart failure occur without clear etiology and are called idiopathic.

CHF is also typically accompanied by alterations in one or more aspects of β-adrenergic neurohumoral function; see Feldman et al., *J. Clin. Invest.*, 82:189–197, (1988); Bristow et al., *N. Engl. J. Med.*, 307:205–211, (1982); Bristow et al., *Circ. Res.*, 59:297–309 (1986); Ungerer et al., *Circulation*, 87: 454–461 (1993); Bristow et al., *J. Clin. Invest.*, 92: 2737–2745 (1993); Calderone et al., *Circ. Res.*, 69:332–343 (1991); Marzo et al., *Circ. Res.*, 69:1546–1556 (1991); C. S. Liang et al., *J. Clin. Invest.*, 84: 1267–1275 (1989); Roth et al., *J. Clin. Invest.*, 91: 939–949 (1993); Hadcock and Malbon, *Proc. Natl. Acad. Sci.*, 85:5021–5025 (1988); Hadcock et al., *J. Biol. Chem.*, 264: 19928–19933 (1989); Mahan, et al., *Proc. Natl. Acad. Sci. USA*, 82:129–133 (1985); Hammond et al., *Circulation*, 85:269–280 (1992);

Neumann et al., *Lancet*, 2: 936–937 (1988); Urasawa et al., *G Proteins: Signal Transduction and Disease*, Academic Press, London. 44–85 (1992); Bohm, *Mol. Cell Biochem.*, 147: 147–160 (1995); Eschenhage et al., *Z. Kardiol*, 81 (Suppl 4): 33–40 (1992); and Yamamoto et al., *J. Mol. Cell.*, 26: 617–626 (1994). There are other references regarding various adenylyl cyclase enzymes. see, Yoshimura et al., *Proc. Natl. Acad. Sci. USA*, 89:6716–6720 (1992); Ishikawa et al., *J. Biol. Chem.*, 267:13553–13557 (1992); Fujita et al., *Circulation*, 90(4): Part 2) (1994); Krupinski et al., *J. Biol. Chem.*, 267:24858–24862 (1992); Ishikawa et al., *J. Clin. Invest*, 93:2224–2229 (1994); Katsushika et al., *Proc. Natl. Acad. Sci. USA*, 89:8774–8778 (1992); Wallach et al., *FEBS Lett.*, 338:257–263 (1994); Watson et al., *J. Biol. Chem.*, 269:28893–28898 (1994); Manolopoulos et al., *Biochem. Biophys. Res. Commun.*, 208:323–331 (1995); Yu et al., *FEBS Lett*, 374:89–94 (1995); and Chen et al., *J. Biol. Chem.*, 270:27525–27530 (1995).

Differential changes in the left and right ventricular adenylyl cyclase activities have been demonstrated in congestive heart failure patients (see, for example, Sethi, Rajat, et al., APStracts 3:0403H, 1196). The Sethi abstract reports that the levels of adenylyl cyclase in crude membranes from both left and right ventricles was determined upon occluding the left coronary artery in rats for 4, 8 and 16 weeks. The adenylyl cyclase activity in the presence of isoproterenol was decreased in the uninfarcted (viable) left ventricle and increased in the right ventricle subsequent to myocardial infarction. The catalytic activity of adenylyl cyclase was depressed in the viable left ventricle but was unchanged in the right ventricle. In comparison to sham controls, the basal, as well as NaF-, forskolin-, and Gpp(NH)p-stimulated adenylyl cyclase activities, were decreased in the left ventricle and increased in the right ventricle of the experimental animals. Opposite alterations in the adenylyl cyclase activities in left and right ventricles from infarcted animals were also seen when two types of purified sarcolemmal preparations were employed. These changes in adenylyl cyclase activities in the left and right ventricles were dependent upon the degree of heart failure. Furthermore, cyclic AMP contents were higher in the right ventricle and lower in the left ventricle from infarcted animals injected with saline, isoproterenol or forskolin in comparison to the controls. The results suggest differential changes in the viable left and right ventricles with respect to adenylyl cyclase activities during the development of congestive heart failure due to myocardial infarction. Accordingly, inhibiting adenylyl cyclase would be helpful in treating congestive heart failure.

Fibroproliferative vasculopathy includes restenosis following coronary bypass surgery and PTCA (percutaneous transluminal coronary angioplasty), allograft arteriosclerosis in chronic allograft rejection, diabetic angiopathy and all forms of common arteriosclerosis. Vascular intimal dysplasia and remodeling are characteristic features of reinjury following balloon angioplasty, coronary bypass surgery (Holmes et al. 1984; Holmes et al. 1988) and in chronic allograft rejection (Lemstrom and Koskinen, 1997; Hayry et al. 1993). An initial response to vascular injury is inflammatory and involves attraction of lymphocytes, macrophages and thrombocytes to the site of injury and secretion of cytokines, eicosanoids and growth factors (Ross 1993). Under the influence of growth factors and cytokines, smooth muscle cells (SMC) proliferate and migrate from the media to the intima and contribute to intimal hyperplasia and stenosis. Some key mediators of SMC proliferation and migration are IL-1, TNF alpha, PDGF, IGF1, bFGF, EGF, TGFβ and VEGF (Asahara et al. 1995; Bornfeldt et al. 1994; Ferns et al. 1991; Libby and Galis 1995, Galis et al. 1995; Gronwald et al. 1989; Hancock et al. 1994; Hayry et al. 1995; Lindner and Reidny 1991; Myllarnemi et al. 1997; Nabel et al. 1993; Shi et al. 1996; Tanaka et al. 1996) and the matrix metalloproteinases in SMC locomotion through the extracellular matrix (Bendeck et al. 1996; Galis et al. 1995).

SUMMARY OF THE INVENTION

The present invention relates to potent new adenine based inhibitors of adenylyl cyclase of formula (I):

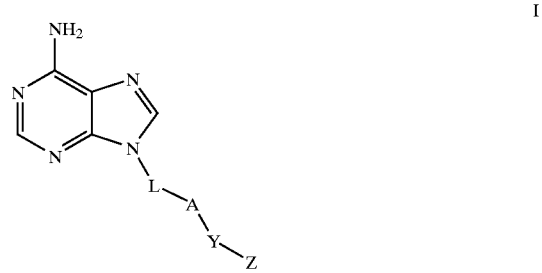

I wherein:
A is a direct link or A is divalent member selected from the group consisting of:
phenyl, thienyl, furanyl, pyrrolyl, indolyl,

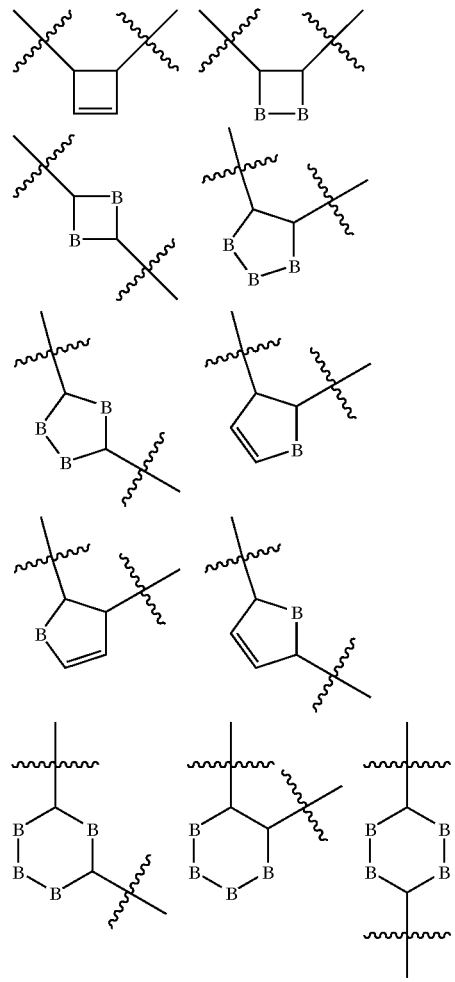

-continued

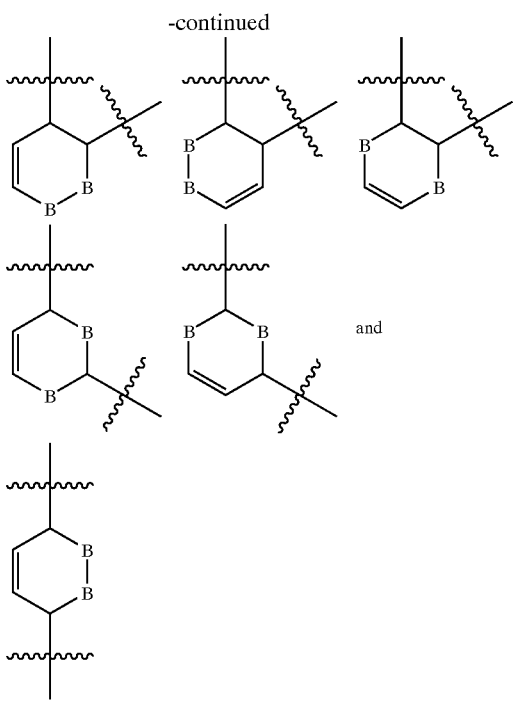

wherein
each B is independently —C(—R$^1$)(—R$^2$)—, —O— or —N(—J—R$^3$)—, and wherein only one ring B is either O or —N(—J—R$^3$)—;
m and n are each independently an integer from 0–4;
q is an integer from 0 to 8;
Y is —(CH$_2$)$_q$—, —(CH$_2$)$_m$O—, (CH$_2$)$_m$—N(—J$^1$—)—R$^4$;
Z is —(CH$_2$)$_n$—C(=O)—NHOH and —(CH$_2$)$_n$COOH;
L is —(CH$_2$)$_q$—, —(CH$_2$)$_m$O—, —(CH$_2$)$_m$—N(—J$^2$—)—R$^5$;
J, J$^1$ and J$^2$ are each independently —C(=O)— or a direct link;
R$^1$ is H, —N(—J$^3$—R$^6$)(—J$^4$—R$^7$) or —O—J$^5$—R$^8$;
wherein J$^3$, J$^4$ and J$^5$ are each independently —C(=O)—, a direct link, or at least one of J$^3$ and J$^4$ is a direct link;
R$^2$ is H, —N(—J$^6$—R$^9$)(—J$^7$—R$^{10}$) or —O—J$^8$—R$^{11}$;
wherein J$^6$, J$^7$ and J$^8$ are each independently —C(=O)—, a direct link, or at least one of J$^6$ and J$^7$ is a direct link;
R$^3$ is H, C$_1$–C$_8$ alkyl, CF$_3$, or —O—R$^{12}$;
R$^4$ is H, C$_1$–C$_8$ alkyl, CF$_3$, or —O—R$^{13}$;
R$^5$ is H, C$_1$–C$_8$ alkyl, CF$_3$, or —O—R$^{14}$;
R$^6$ is H, C$_1$–C$_8$ alkyl, CF$_3$, or —O—R$^{15}$;
R$^7$ is H, C$_1$–C$_8$ alkyl, CF$_3$, or —O—R$^{16}$;
R$^8$ is H, C$_1$–C$_8$ alkyl, CF$_3$, or —O—R$^{17}$;
R$^9$ is H, C$_1$–C$_8$ alkyl, CF$_3$, or —O—R$^{18}$;
R$^{10}$ is H, C$_1$–C$_8$ alkyl, CF$_3$, or —O—R$^{19}$;
R$^{11}$ is H, C$_1$–C$_8$ alkyl, CF$_3$, or —O—R$^{20}$;
R$^{12}$, R$^{13}$, R$^{14}$, R$^{15}$, R$^{16}$, R$^{17}$, R$^{18}$, R$^{19}$ and R$^{20}$ are each independently C$_1$–C$_4$ alkyl, cycloalkyl or benzyl;
and all pharmaceutically acceptable isomers, salts, hydrates, solvates and prodrug derivatives thereof.

Another aspect of the invention relates to pharmaceutical compositions comprising the compound of formula I and a pharmaceutically acceptable carrier or diluent.

The adenine derivatives of the present invention inhibit adenylyl cyclases directly and are thus useful, among other uses, to inhibit or prevent a patient's fibroproliferative vasculopathy following vascular injury or a vascular surgical operation.

Another aspect of the present invention relates to a method for administering to a patient in need thereof an effective amount of an adenylyl cyclase inhibitory compound according to the invention and subsequent to the diagnosis of congestive heart failure, the occurrence of a vascular injury, or subsequent to a vascular surgical operation.

Another aspect of the invention relates to administration of the compound, either chronically after the diagnosis of congestive heart failure or for one to two weeks after the occurrence of a vascular injury or surgical operation. The amount of compound administered is an amount effective to treat or prevent a patient's congestive heart failure or fibroproliferative vasculopathy such as chronic allograft rejection or vascular restenosis following vascular trauma.

Still, another aspect of the present invention relates to adenylyl cyclase inhibitory compounds according to the invention which are useful in the preparation of covalent affinity probes and affinity chromatography matrices. Such inhibitory compounds are important to many aspects of biology, biochemistry, pharmacology, and therapeutics and will find use in the treatment of various diseases and, more specifically, treatment of cardiovascular diseases.

Other aspects, objects, features and advantages of the present invention would be apparent to one of ordinary skill in the art from the following detailed description illustrating the preferred embodiments of the invention.

DETAILED DESCRIPTION OF THE INVENTION

Definitions

In accordance with the present invention and as used herein, the following terms are defined with the following meanings, unless explicitly stated otherwise.

The term "alkenyl" refers to a trivalent straight chain or branched chain unsaturated aliphatic radical. The term "alkinyl" (or "alkynyl") refers to a straight or branched chain aliphatic radical that includes at least two carbons joined by a triple bond. If no number of carbons is specified alkenyl and alkinyl each refer to radicals having from 2–12 carbon atoms.

The term "alkyl" refers to saturated aliphatic groups including straight-chain, branched-chain and cyclic groups having the number of carbon atoms specified, or if no number is specified, having up to 12 carbon atoms. The term "cycloalkyl" as used herein refers to a mono-, bi-, or tricyclic aliphatic ring having 3 to 14 carbon atoms and preferably 3 to 7 carbon atoms.

As used herein, the terms "carbocyclic ring structure" and "C$_{3-16}$ carbocyclic mono, bicyclic or tricyclic ring structure" or the like are each intended to mean stable ring structures having only carbon atoms as ring atoms wherein the ring structure is a substituted or unsubstituted member selected from the group consisting of: a stable monocyclic ring which is aromatic ring ("aryl") having six ring atoms; a stable monocyclic non-aromatic ring having from 3 to 7 ring atoms in the ring; a stable bicyclic ring structure having a total of from 7 to 12 ring atoms in the two rings wherein the bicyclic ring structure is selected from the group consisting of ring structures in which both of the rings are aromatic, ring structures in which one of the rings is aromatic and ring structures in which both of the rings are non-aromatic; and a stable tricyclic ring structure having a total of from 10 to 16 atoms in the three rings wherein the tricyclic ring structure is selected from the group consisting of: ring structures in which three of the rings are aromatic, ring structures in which two of the rings are aromatic and ring structures in which three of the rings are non-aromatic. In each case, the non-aromatic rings when present in the monocyclic, bicyclic or tricyclic ring structure may independently be saturated, partially saturated or fully saturated. Examples of such carbocyclic ring structures include, but are not limited to, cyclopropyl, cyclobutyl, cyclopentyl, cyclohexyl, adamantyl, cyclooctyl, [3.3.0]bicyclooctane, [4.3.0]bicyclononane, [4.4.0]bicyclodecane (decalin), 2.2.2] bicyclooctane, fluorenyl, phenyl, naphthyl, indanyl, adamantyl, or tetrahydronaphthyl (tetralin). Moreover, the ring structures described herein may be attached to one or more indicated pendant groups via any carbon atom which results in a stable structure. The term "substituted" as used in conjunction with carbocyclic ring structures means that hydrogen atoms attached to the ring carbon atoms of ring structures described herein may be substituted by one or more of the substituents indicated for that structure if such substitution(s) would result in a stable compound.

The term "aryl" which is included with the term "carbocyclic ring structure" refers to an unsubstituted or substituted aromatic ring, substituted with one, two or three substituents selected from lower alkoxy, lower alkyl, lower alkylamino, hydroxy, halogen, cyano, hydroxyl, mercapto, nitro, thioalkoxy, carboxaldehyde, carboxyl, carboalkoxy and carboxamide, including but not limited to carbocyclic aryl, heterocyclic aryl, and biaryl groups and the like, all of which may be optionally substituted. Preferred aryl groups include phenyl, halophenyl, loweralkylphenyl, napthyl, biphenyl, phenanthrenyl and naphthacenyl.

The term "arylalkyl" which is included with the term "carbocyclic aryl" refers to one, two, or three aryl groups having the number of carbon atoms designated, appended to an alkyl group having the number of carbon atoms designated. Suitable arylalkyl groups include, but are not limited to, benzyl, picolyl, naphthylmethyl, phenethyl, benzyhydryl, trityl, and the like, all of which may be optionally substituted.

As used herein, the term "heterocyclic ring" or "heterocyclic ring system" is intended to mean a substituted or unsubstituted member selected from the group consisting of stable monocyclic ring having from 5–7 members in the ring itself and having from 1 to 4 hetero ring atoms selected from the group consisting of N, O and S; a stable bicyclic ring structure having a total of from 7 to 12 atoms in the two rings wherein at least one of the two rings has from 1 to 4 hetero atoms selected from N, O and S, including bicyclic ring structures wherein any of the described stable monocyclic heterocyclic rings is fused to a hexane or benzene ring; and a stable tricyclic heterocyclic ring structure having a total of from 10 to 16 atoms in the three rings wherein at least one of the three rings has from 1 to 4 hetero atoms selected from the group consisting of N, O and S. Any nitrogen and sulfur atoms present in a heterocyclic ring of such a heterocyclic ring structure may be oxidized. Unless indicated otherwise the terms "heterocyclic ring" or "heterocyclic ring system" include aromatic rings, as well as non-aromatic rings which can be saturated, partially saturated or fully saturated non-aromatic rings. Also, unless indicated otherwise the term "heterocyclic ring system" includes ring structures wherein all of the rings contain at least one hetero atom as well as structures having less than all of the rings in the ring structure containing at least one hetero atom, for example bicyclic ring structures wherein one ring is a benzene ring and one of the rings has one or more hetero atoms are included within the term "heterocyclic ring systems" as well as bicyclic ring structures wherein each of the two rings has at least one hetero atom. Moreover, the ring structures described herein may be attached to one or more indicated pendant groups via any hetero atom or carbon atom which results in a stable structure. Further, the term "substituted" means that one or more of the hydrogen atoms on the ring carbon atom(s) or nitrogen atom(s) of the each of the rings in the ring structures described herein may be replaced by one or more of the indicated substituents if such replacement(s) would result in a stable compound. Nitrogen atoms in a ring structure may be quatemized, but such compounds are specifically indicated or are included within the term "a pharmaceutically acceptable salt" for a particular compound. When the total number of O and S atoms in a single heterocyclic ring is greater than 1, it is preferred that such atoms not be adjacent to one another. Preferably, there are no more than one O or S ring atoms in the same ring of a given heterocyclic ring structure.

Examples of monocyclic and bicyclic heterocyclic ring systems, in alphabetical order, are acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalinyl, carbazolyl, 4aH-carbazolyl, carbolinyl, chromanyl, chromenyl, cinnolinyl, decahydroquinolinyl, 2H,6H-1,5,2-dithiazinyl, dihydrofuro [2,3-b]tetrahydrofuran, furanyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyroazolidinyl, pyrazolinyl, pyrazolyl, pyridazinyl, pryidooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl and xanthenyl. Preferred heterocyclic ring structures include, but are not limited to, pyridinyl, furanyl, thienyl, pyrrolyl, pyrazolyl, pyrrolidinyl, imidazolyl, indolyl, benzimidazolyl, 1H-indazolyl, oxazolinyl, or isatinoyl. Also included are fused ring and spiro compounds containing, for example, the above heterocyclic ring structures.

As used herein the term "aromatic heterocyclic ring system" has essentially the same definition as for the monocyclic and bicyclic ring systems except that at least one ring of the ring system is an aromatic heterocyclic ring or the bicyclic ring has an aromatic or non-aromatic heterocyclic ring fused to an aromatic carbocyclic ring structure.

The terms "halo" or "halogen" as used herein refer to Cl, Br, F or I substituents. The term "haloalkyl", and the like, refer to an aliphatic carbon radicals having at least one hydrogen atom replaced by a Cl, Br, F or I atom, including mixtures of different halo atoms. Trihaloalkyl includes trifluoromethyl and the like as preferred radicals, for example.

The term "alkylene chain" refers to straight or branched chain unsaturated divalent radical consisting solely of carbon and hydrogen atoms containing no unsaturation and having from one to six carbon atoms, e.g., methylene, ethylene, propylene, butylenes, and the like. The term "methylene" refers to —$CH_2$—. The term "Bu" refers to "butyl" or —$CH_2CH_2CH_2CH_2$—; the term "Ph" refers to "phenyl"; the term "Me" refers to "methyl" or —$CH_3$; the term "Et" refers to "ethyl" or —$CH_2CH_3$; the term "Bu(t)" or "t-Bu" refers to "tert-butyl" or —$C(CH_3)_4$.

The term "pharmaceutically acceptable salts" includes salts of compounds derived from the combination of a compound and an organic or inorganic acid. These compounds are useful in both free base and salt form. In practice, the use of the salt form amounts to use of the base form; both acid and base addition salts are within the scope of the present invention.

"Pharmaceutically acceptable acid addition salt" refers to salts retaining the biological effectiveness and properties of the free bases and which are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicyclic acid and the like.

"Pharmaceutically acceptable base addition salts" include those derived from inorganic bases such as sodium, potassium, lithium, ammonium, calcium, magnesium, iron, zinc, copper, manganese, aluminum salts and the like. Particularly preferred are the ammonium, potassium, sodium, calcium and magnesium salts. Salts derived from pharmaceutically acceptable organic nontoxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, polyamine resins and the like. Particularly preferred organic nontoxic bases are isopropylamine, diethylamine, ethanolamine, trimethamine, dicyclohexylamine, choline, and caffeine.

"Biological property" for the purposes herein means an in vivo effector or antigenic function or activity that is directly or indirectly performed by a compound of this invention that are often shown by in vitro assays. Effector functions include receptor or ligand binding, any enzyme activity or enzyme modulatory activity, any carrier binding activity, any hormonal activity, any activity in promoting or inhibiting adhesion of cells to an extracellular matrix or cell surface molecules, or any structural role. Antigenic functions include possession of an epitope or antigenic site that is capable of reacting with antibodies raised against it.

Preferred Embodiments

In one preferred embodiment the present invention relates to a compound of the formula (I):

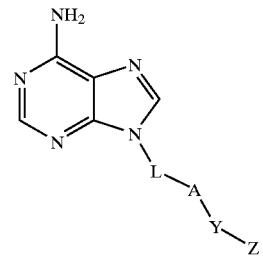

I wherein:

A is a direct link or A is divalent member selected from the group consisting of:
phenyl, thienyl, furanyl, pyrrolyl, indolyl,

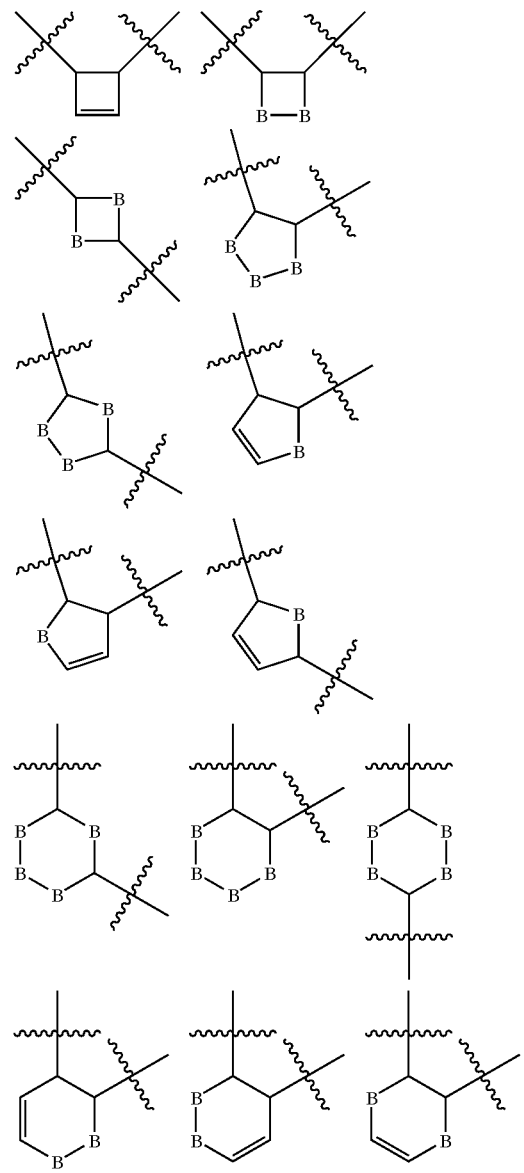

-continued

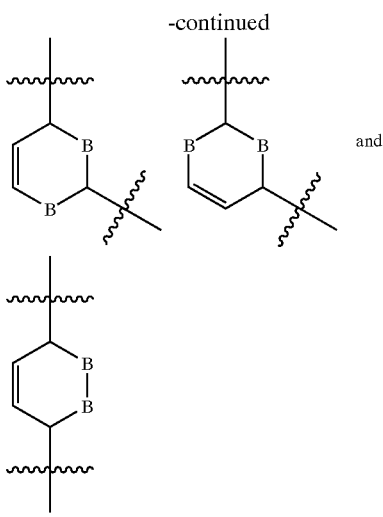

wherein each B is independently —C(—R$^1$)(—R$^2$)—, —O— or —N(—J—R$^3$)—, and wherein only one ring B is either O or —N(—J—R$^3$)—;

m and n are each independently an integer from 0–4;

q is an integer from 0 to 8;

Y is —(CH$_2$)$_q$—, —(CH$_2$)$_m$O—, —(CH$_2$)$_m$—N(—J$^1$—)—R$^4$;

Z is —(CH$_2$)$_n$—C(=O)—NHOH and —(CH$_2$)$_n$COOH;

L is —(CH$_2$)$_q$—, —(CH$_2$)$_m$O—, —(CH$_2$)$_m$—N—(—J$^2$—)—R$^5$;

J, J$^1$ and J$^2$ are each independently —C(=O)— or a direct link;

R$^1$ is H, —N(—J$^3$—R$^6$)(—J$^4$—R$^7$) or —O—J$^5$—R$^8$, wherein J$^3$, J$^4$ and J$^5$ are each independently —C(=O)— or a direct link, and at least one of J$^3$ and J$^4$ is a direct link;

R$^2$ is H, —N(—J$^6$—R$^9$)(—J$^7$—R$^{10}$) or —O—J$^8$—R$^{11}$, wherein J$^6$, J$^7$ and J$^8$ are each independently a —C(=O)— or a direct link, and at least one of J$^6$ and J$^7$ is a direct link;

R$^3$ is H, C$_1$–C$_8$ alkyl, CF$_3$, or —O—R$^{12}$;

R$^4$ is H, C$_1$–C$_8$ alkyl, CF$_3$, or —O—R$^{13}$;

R$^5$ is H, C$_1$–C$_8$ alkyl, CF$_3$, or —O—R$^{14}$;

R$^6$ is H, C$_1$–C$_8$ alkyl, CF$_3$, or —O—R$^{15}$;

R$^7$ is H, C$_1$–C$_8$ alkyl, CF$_3$, or —O—R$^{16}$;

R$^8$ is H, C$_1$–C$_8$ alkyl, CF$_3$, or —O—R$^{17}$;

R$^9$ is H, C$_1$–C$_8$ alkyl, CF$_3$, or —O—R$^{18}$;

R$^{10}$ is H, C$_1$–C$_8$ alkyl, CF$_3$, or —O—R$^{19}$;

R$^{11}$ is H, C$_1$–C$_8$ alkyl, CF$_3$, or —O—R$^{20}$;

R$^{12}$, R$^{13}$, R$^{14}$, R$^{15}$, R$^{16}$, R$^{17}$, R$^{18}$, R$^{19}$ and R$^{20}$ are each independently a C$_1$–C$_4$ alkyl, cycloalkyl or benzyl;

and all pharmaceutically acceptable isomers, salts, hydrates, solvates and prodrug derivatives thereof.

The pharmaceutically acceptable salts of the compounds according to formula (I) include pharmaceutically acceptable acid addition salts, metal salts, ammonium salts, organic amine addition salts, amino acid addition salts, etc. Examples of the pharmaceutically acceptable acid addition salts of the compounds of formula (I) are inorganic acid addition salts such as hydrochloride, sulfate and phosphate, and organic acid addition salts such as acetate, maleate, fumarate, tartrate, citrate and methanesulfonate. Examples of the pharmaceutically acceptable metal salts are alkali metal salts such as sodium salt and potassium salt, alkaline earth metal salts such as magnesium salt and calcium salt, aluminum salt and zinc salt. Examples of the pharmaceutically acceptable ammonium salts are ammonium salt and tetramethyl ammonium salt. Examples of the pharmaceutically acceptable organic amine addition salts include heterocyclic amine salts such as morpholine and piperidine salts. Examples of the pharmaceutically acceptable amino acid addition salts are salts with lysine, glycine and phenylalanine.

This invention also encompasses prodrug derivatives of the compounds contained herein. The term "prodrug" refers to a pharmacologically inactive derivative of a parent drug molecule that requires biotransformation, either spontaneous or enzymatic, within the organism to release the active drug. Prodrugs are variations or derivatives of the compounds of this invention which have groups cleavable under metabolic conditions. Prodrugs become the compounds of the invention which are pharmaceutically active in vivo, when they undergo solvolysis under physiological conditions or undergo enzymatic degradation. Prodrug compounds of this invention may be called single, double, triple etc., depending on the number of biotransformation steps required to release the active drug within the organism, and indicating the number of functionalities present in a precursor-type form. Prodrug forms often offer advantages of solubility, tissue compatibility, or delayed release in the mammalian organism (see, Bundgard, Design of Prodrugs, pp. 7–9, 21–24, Elsevier, Amsterdam 1985 and Silverman, The Organic Chemistry of Drug Design and Drug Action, pp. 352–401, Academic Press, San Diego, Calif., 1992). Prodrugs commonly known in the art include acid derivatives well known to practitioners of the art, such as, for example, esters prepared by reaction of the parent acids with a suitable alcohol, or amides prepared by reaction of the parent acid compound with an amine, or basic groups reacted to form an acylated base derivative. Moreover, the prodrug derivatives of this invention may be combined with other features herein taught to enhance bioavailability. The preparation of pharmaceutically acceptable isomers, solvates or hydrates would be apparent to one of ordinary skill in the art.

In the compounds of this invention, carbon atoms bonded to four non-identical substituents are asymmetric. Accordingly, the compounds may exist as diastereoisomers, enantiomers or mixtures thereof. The syntheses described herein may employ racemates, enantiomers or diastereomers as starting materials or intermediates. Diastereomeric products resulting from such syntheses may be separated by chromatographic or crystallization methods, or by other methods known in the art. Likewise, enantiomeric product mixtures may be separated using the same techniques or by other methods known in the art. Each of the asymmetric carbon atoms, when present in the compounds of this invention, may be in one of two configurations (R or S) and both are within the scope of the present invention.

In a preferred embodiment, the invention provides compounds according to formula (I):

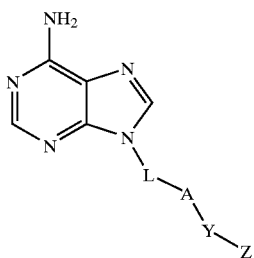

wherein:

A is a direct link, or

A is divalent member selected from the group consisting of:

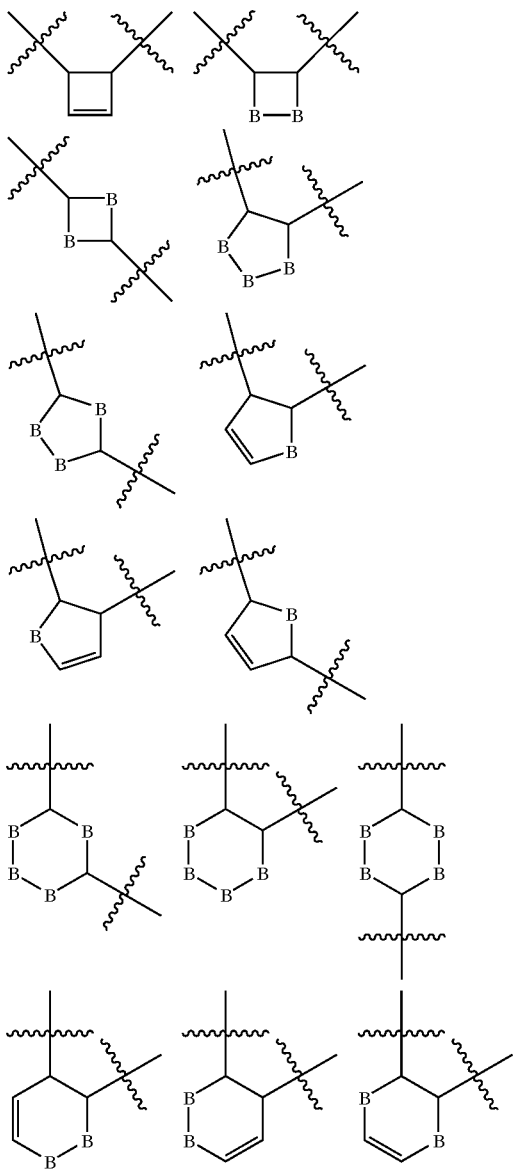

wherein each B is independently —C(—R$^1$)(—R$^2$)—, —O— or —N(—J—R$^3$)—, and wherein only one ring B is either O or —N(—J—R$^3$)—;

m and n are each independently an integer from 0–4;

q is an integer from 0 to 8;

Y is a —(CH$_2$)$_q$— and —(CH$_2$)$_m$O—;

Z is —(CH$_2$)$_n$—C(=O)—NHOH and —(CH$_2$)$_n$COOH;

L is —(CH$_2$)$_q$— and —(CH$_2$)$_m$O—;

J is —C(=O)— or a direct link;

R$^1$ is H or —O—J$^5$—R$^8$, wherein J$^5$ is a —C(=O)— or a direct link;

R$^2$ is a H or —O—J$^8$—R$^{11}$, wherein J$^8$ is —C(=O)— or a direct link;

R$^8$ is H, C$_1$–C$_8$ alkyl, CF$_3$, or —O—R$^{17}$;

R$^{11}$ is H, C$_1$–C$_8$ alkyl, CF$_3$, or —O—R$^{20}$;

R$^{17}$ and R$^{20}$ are each independently a C$_1$–C$_4$ alkyl, cycloalkyl or benzyl;

and all pharmaceutically acceptable isomers, salts, hydrates, solvates and prodrug derivatives thereof.

A further preferred embodiment is a compound of the formula (I):

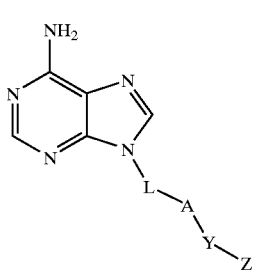

wherein:

A is divalent member selected from the group consisting of:

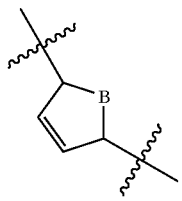 and 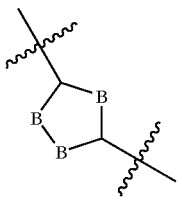

wherein each B is independently the substituted group —C(—R$^1$)(—R$^2$)—;
Y is —(CH$_2$)$_q$— and —(CH$_2$)$_m$O—;
Z is —(CH$_2$)$_n$—C(=O)—NHOH;
L is a —(CH$_2$)$_q$—;
m and n are each independently an integer from 0–4;
q is an integer from 0 to 8; and
R$^1$ and R$^2$ are each H;

and all pharmaceutically acceptable isomers, salts, hydrates, solvates and prodrug derivatives thereof.

The compounds may be prepared using methods and procedures in the Examples presented herein. Starting materials may be made or obtained as described therein as well. Leaving groups such as halogen, lower alkoxy, lower alkylthio, lower alkylsulfonyloxy, arylsulfonyloxy, etc, may be utilized when necessary except for the reaction point, followed by deprotection. Suitable amino protective groups are, for example, those described in T. W. Greene, *Protective Groups in Organic Synthesis*, John Wiley & Sons Inc. (1981), etc., such as ethoxycarbonyl, t-butoxycarbonyl, acetyl and benzyl. The protective groups can be introduced and eliminated according to conventional methods used in organic synthetic chemistry [e.g., T. W. Greene, *Protective Groups in Organic Synthesis*, John Wiley & Sons Inc. (1981)].

In such processes, if the defined groups change under the conditions of the working method or are not appropriate for carrying out the method, the desired compound can be obtained by using the methods for introducing and eliminating protective groups which are conventionally used in organic synthetic chemistry. See, e.g., T. W. Greene, *Protective Groups in Organic Synthesis*, John Wiley & Sons Inc. (1981)], supra. Conversion of functional groups contained in the substituents can be carried out by known methods. See e.g., R. C. Larock, *Comprehensive Organic Transformations* (1989), in addition to the above-described processes, and some of the active compounds of formula I may be utilized as intermediates for further synthesizing novel derivatives according to formula I.

The intermediates and the desired compounds in the processes described above can be isolated and purified by purification methods conventionally used in organic synthetic chemistry, for example, neutralization, filtration, extraction, washing, drying, concentration, recrystallization, and various kinds of chromatography. The intermediates may be subjected to the subsequent reaction without purification.

There may be tautomers for some formula I, and the present invention covers all possible isomers including tautomers and mixtures thereof. Where chiral carbons lend themselves to two different enantiomers, both enantiomers are contemplated as well as procedures for separating the two enantiomers. There may be tautomers for some formula I, and the present invention covers all possible isomers including tautomers and mixtures thereof, the process of making would be apparent to one of ordinary skill in the art. Where chiral carbons lend themselves to two different enantiomers, both enantiomers are contemplated as well as procedures for separating the two enantiomers. In the compounds of this invention, carbon atoms bonded to four non-identical substituents are asymmetric. Accordingly, the compounds may also exist as diastereoisomers, enantiomers or mixtures thereof. The syntheses described herein may employ racemates, enantiomers or diastereomers as starting materials or intermediates. Diastereomeric products resulting from such syntheses may be separated by chromatographic or crystallization methods, or by other methods known in the art. Likewise, enantiomeric product mixtures may be separated using the same techniques or by other methods known in the art. Each of the asymmetric carbon atoms, when present in the compounds of this invention, may be in one of two configurations (R or S) and both are within the scope of the present invention. In the processes described above, the final products may, in some cases, contain a small amount of diastereomeric or enantiomeric products, however these products do not affect their therapeutic or diagnostic application.

In the case where a salt of a compound of formula I is desired and the compound is produced in the form of the desired salt, it can be subjected to purification as such. In the case where a compound of formula I is produced in the free state and its salt is desired, the compound of formula I is dissolved or suspended in a suitable organic solvent, followed by addition of an acid or a base to form a salt.

The following non-limiting reaction Schemes I–XI illustrate preferred embodiments of the invention with respect to making compounds according to the invention.

Scheme I
Alkyl Linked Series
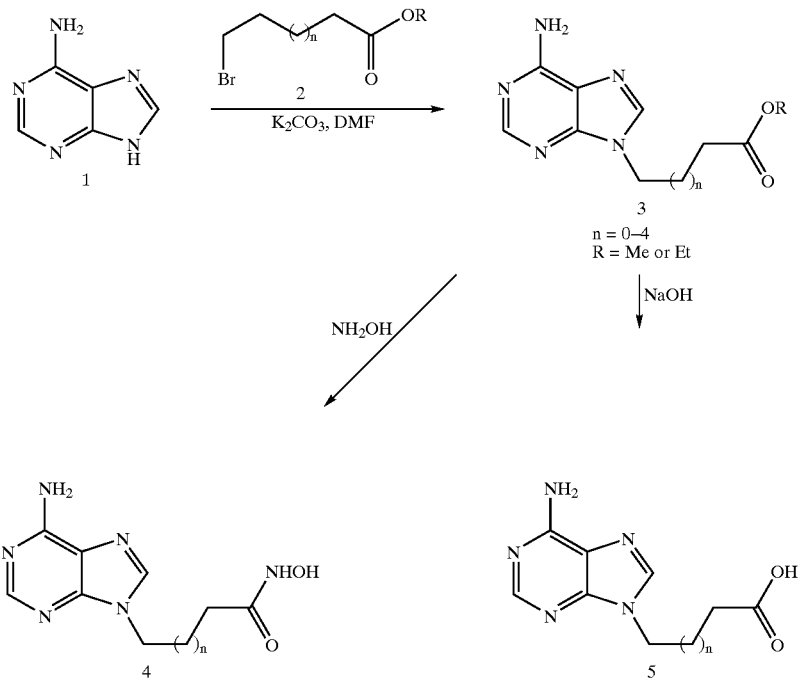
Scheme II
OCH₂ Linked Series
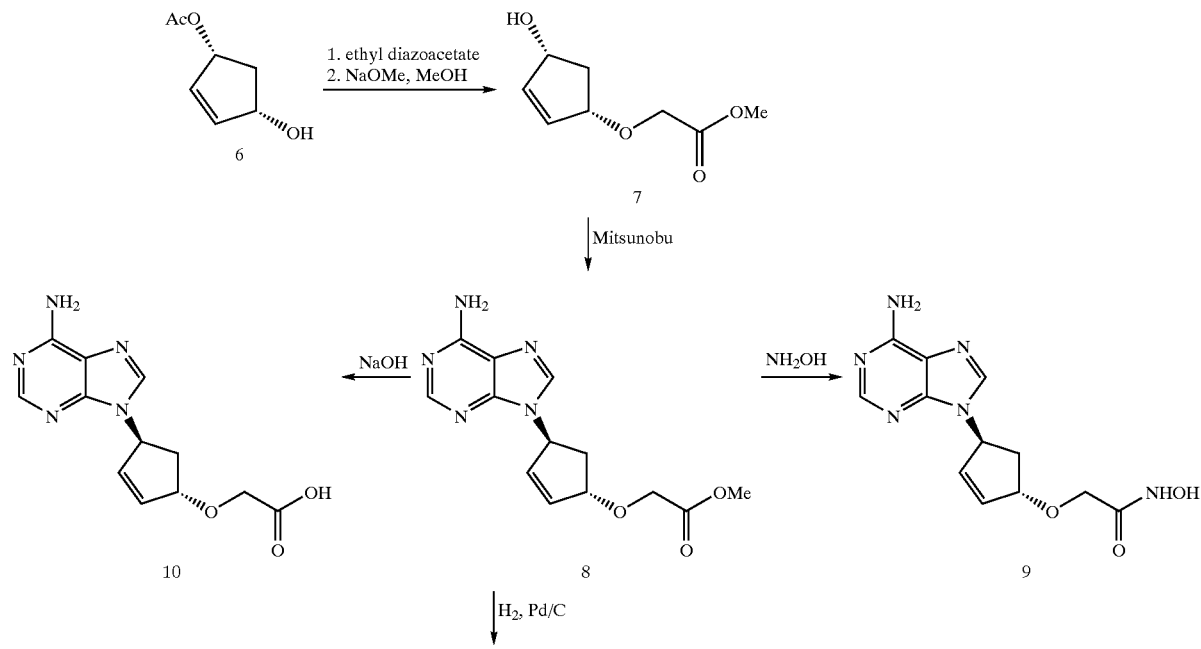

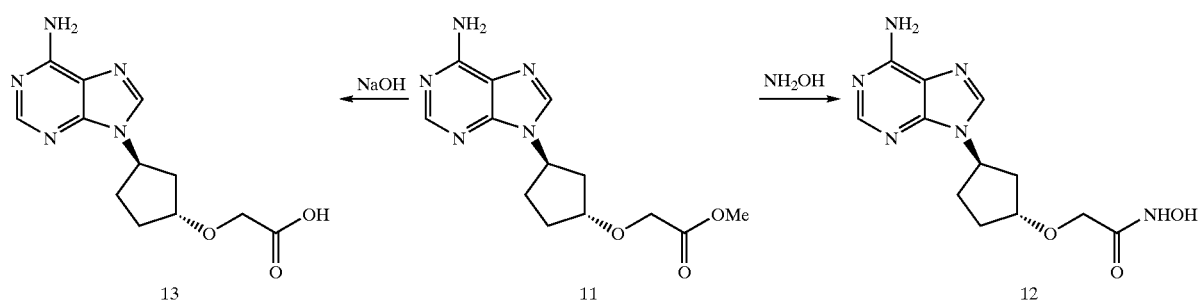
Scheme III
OCH₂ Linked Series
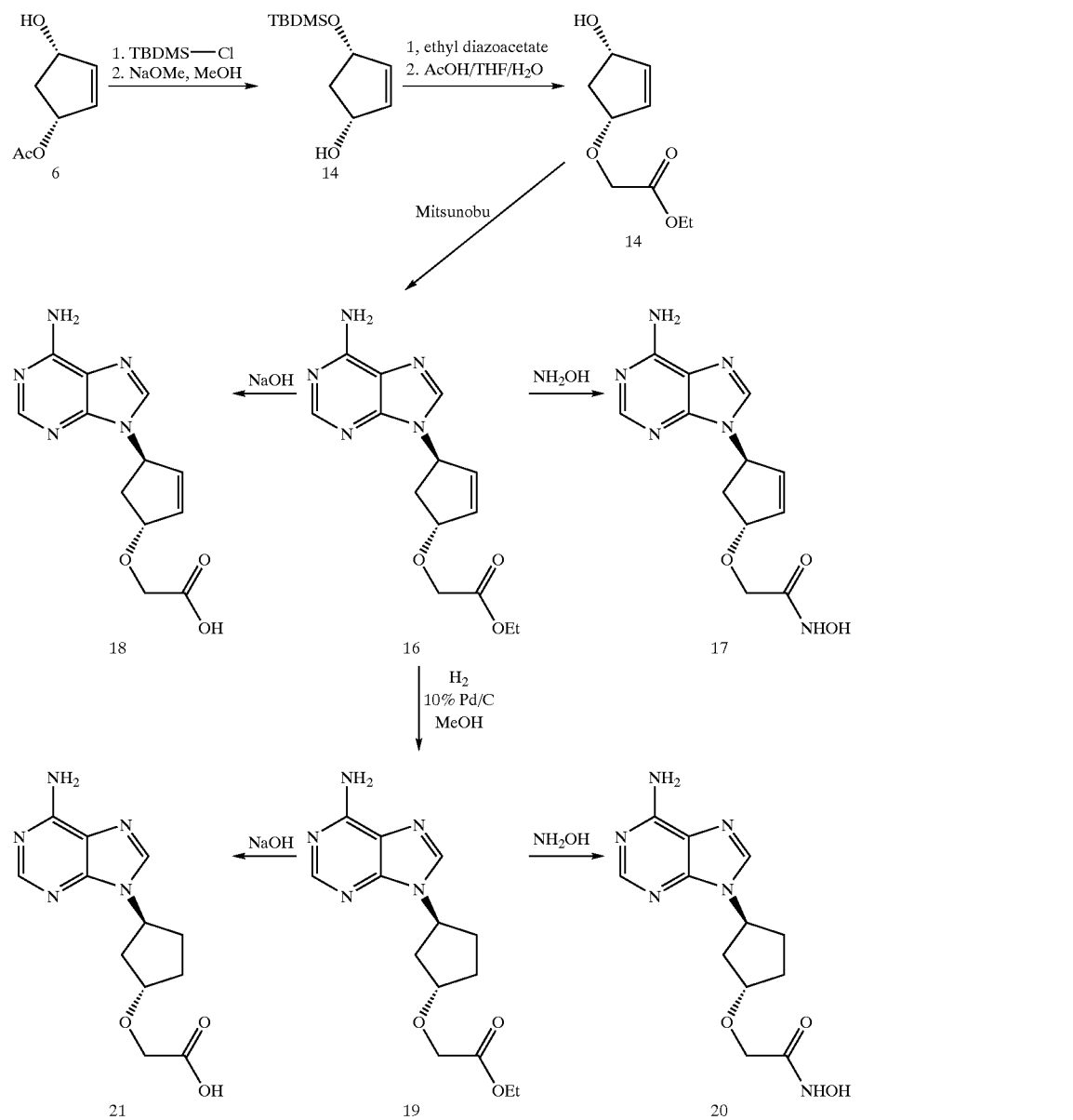

Scheme IV
OCH₂ Linked Series
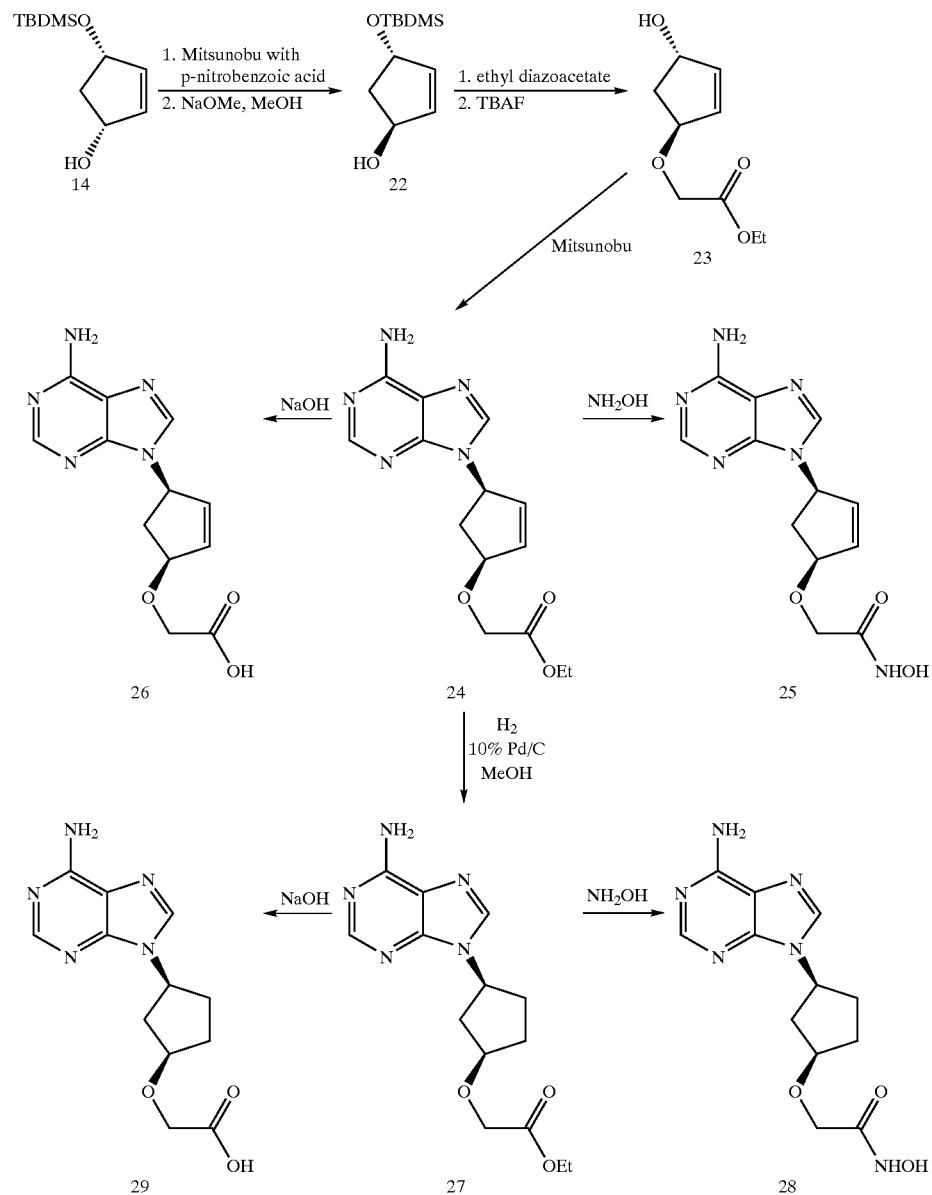
Scheme V
OCH₂ Linked Series
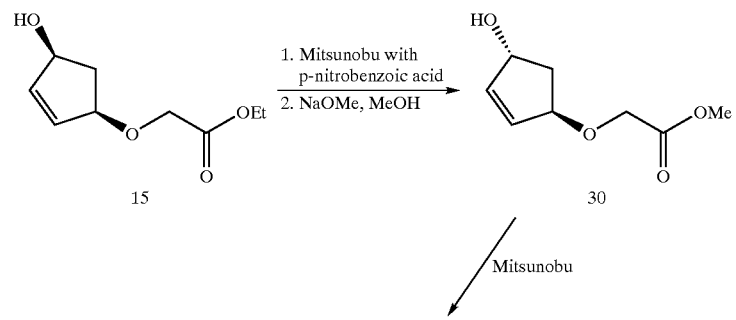

-continued
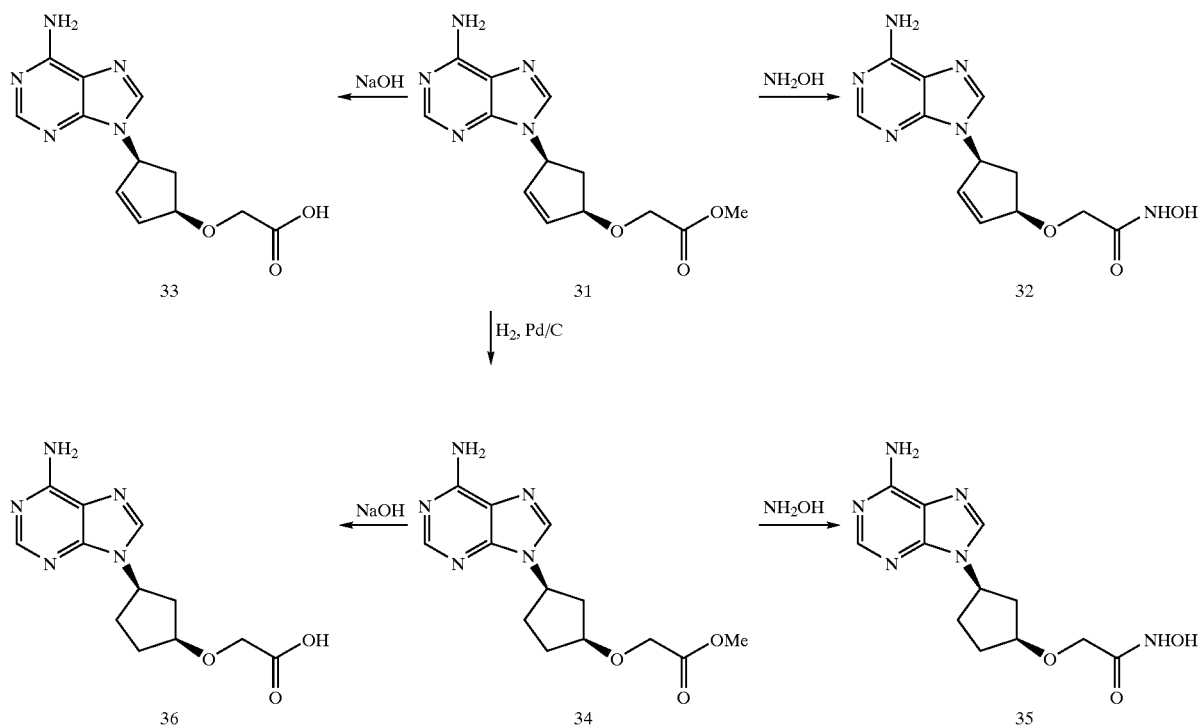
Scheme VI
CH₂ Linked Series
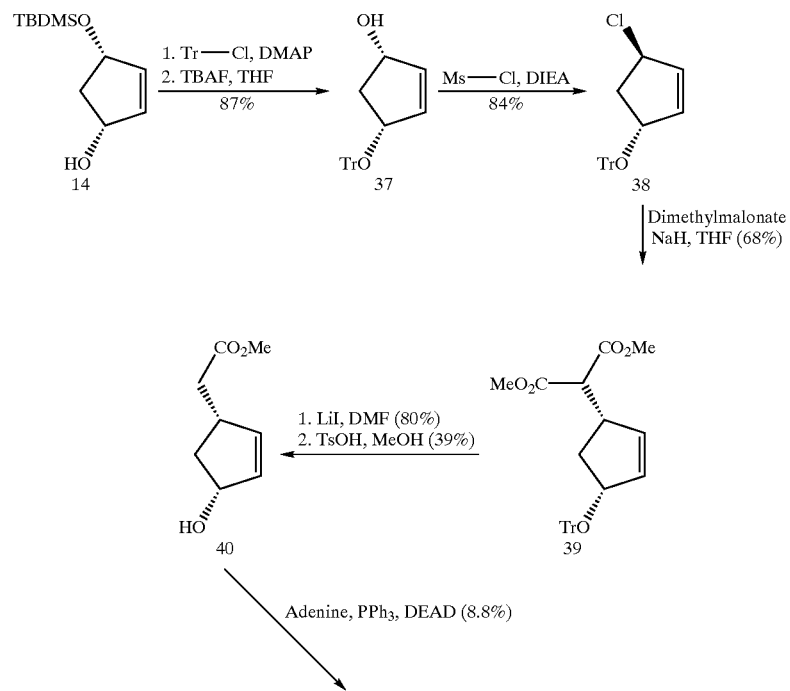

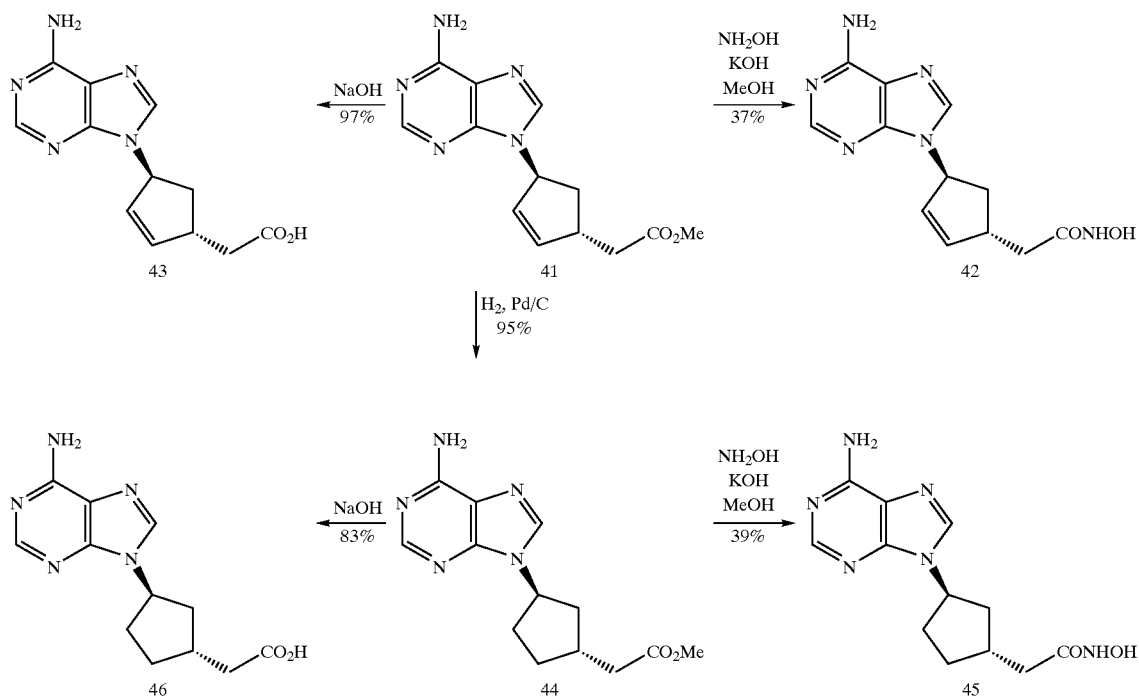
Scheme VII
CH₂ Linked Series
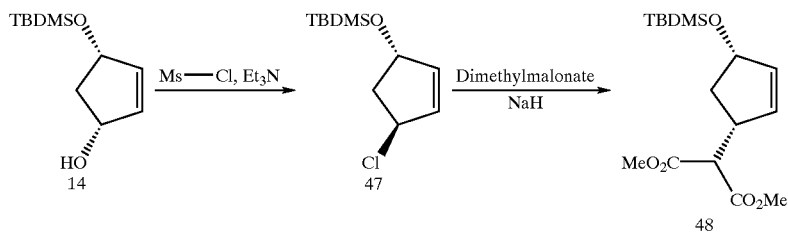
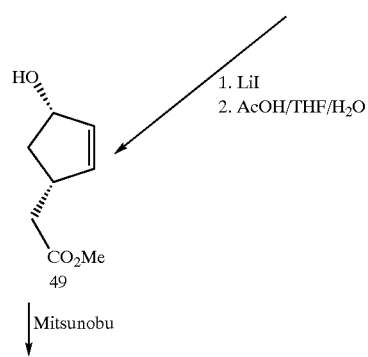

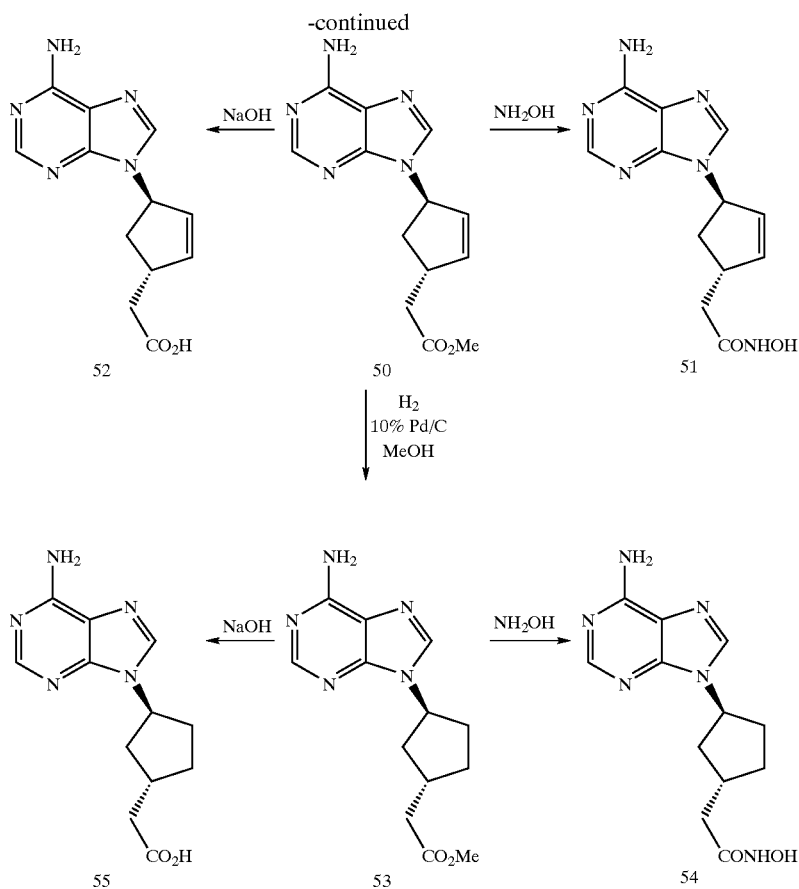
Scheme VIII
CH₂ Linked Series
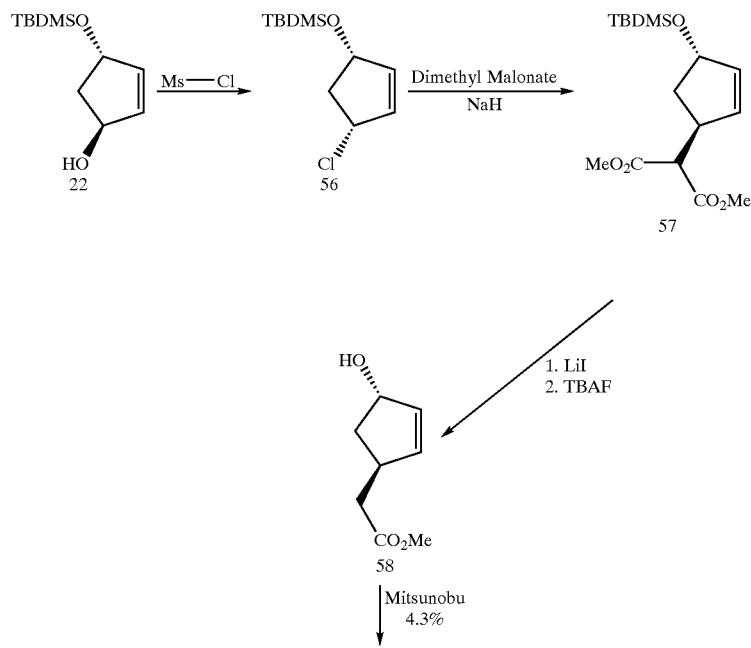

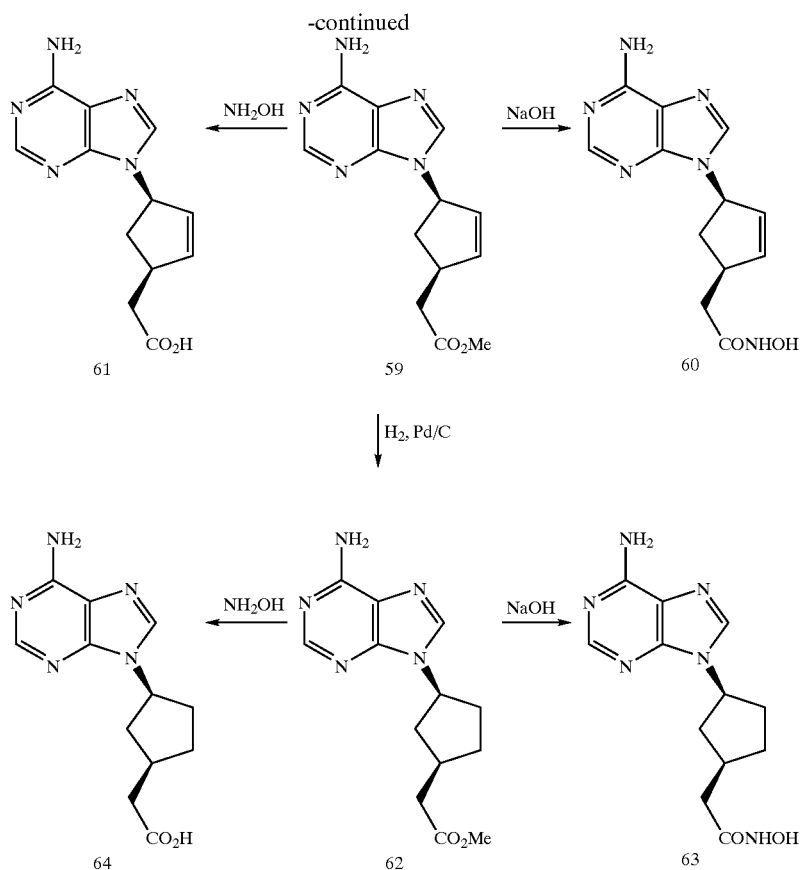
Scheme IX
CH₂ Linked Series
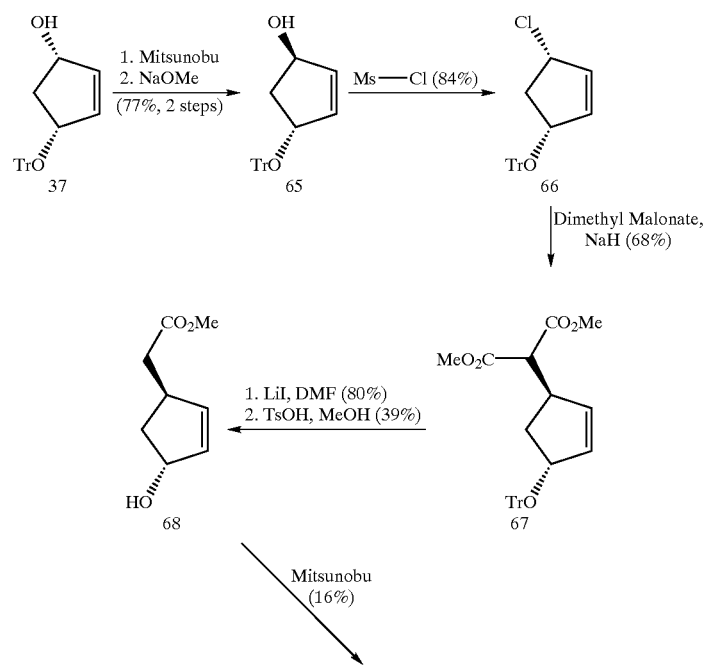

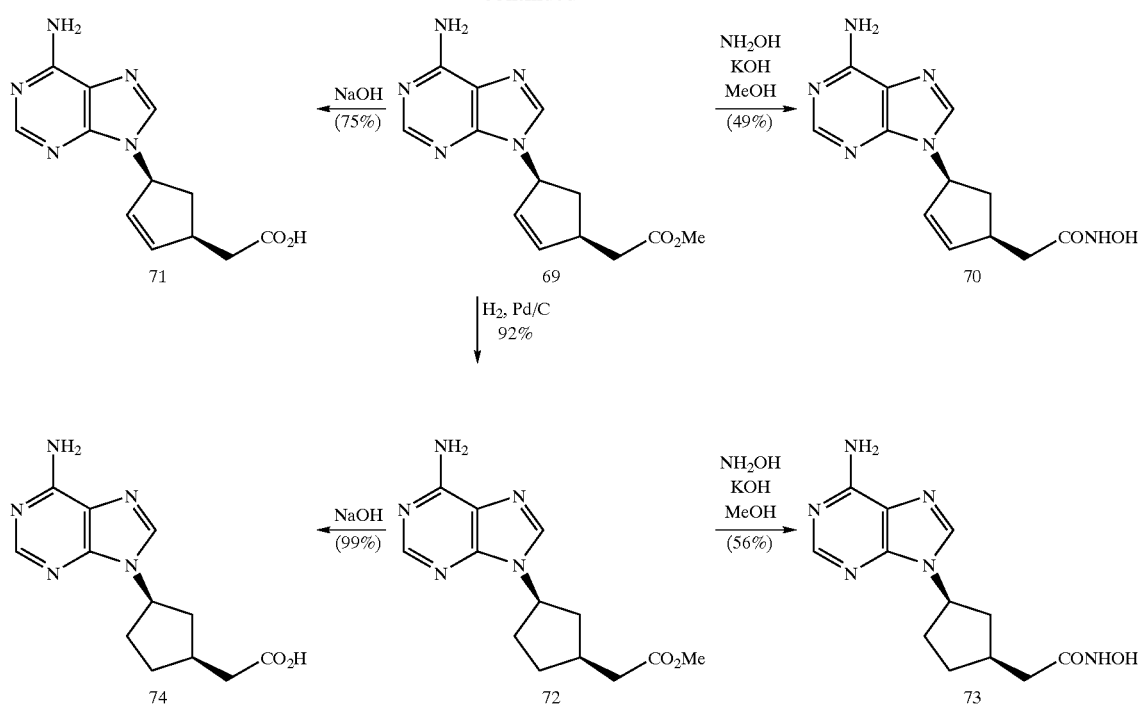
Scheme X (Part I)
Direct Linked Series - Part I
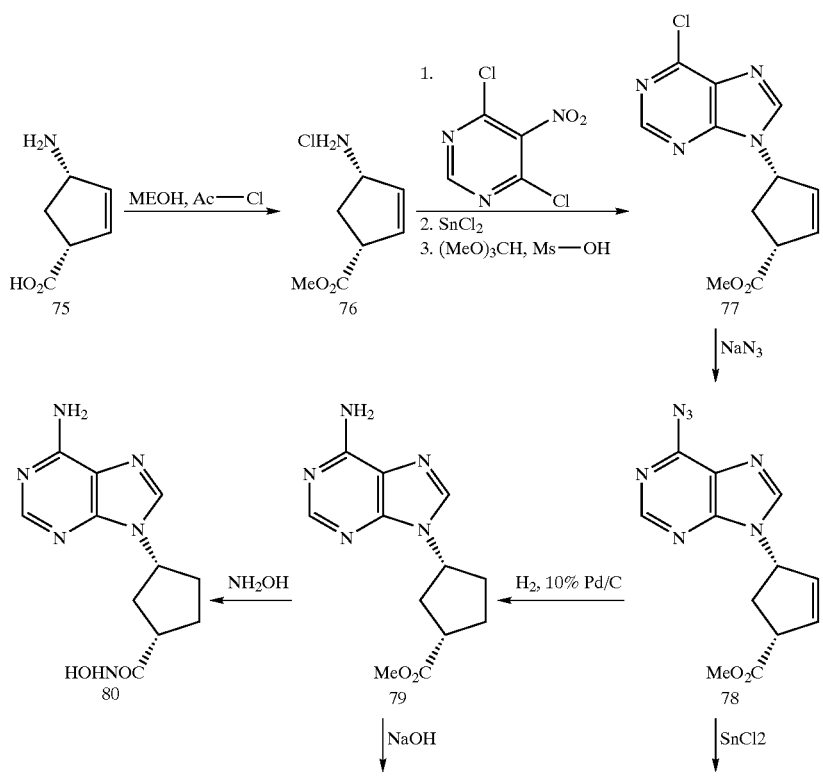

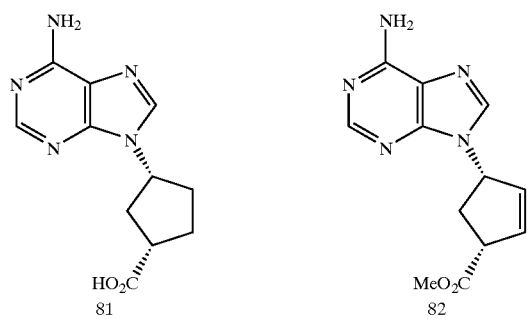

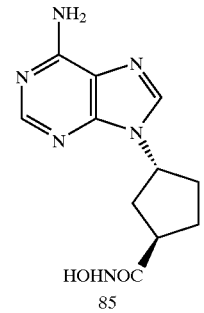

Scheme X (Part II)
Direct Linked Series - Part II

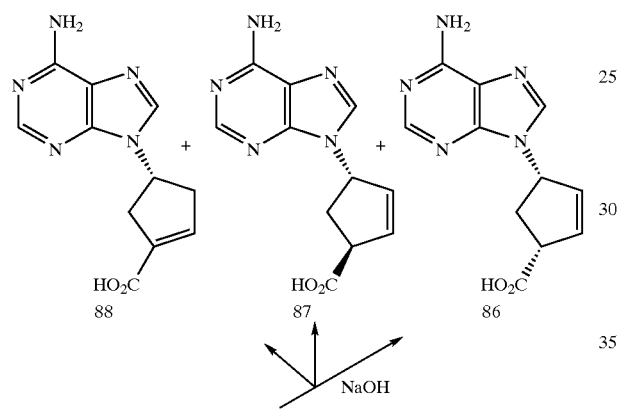

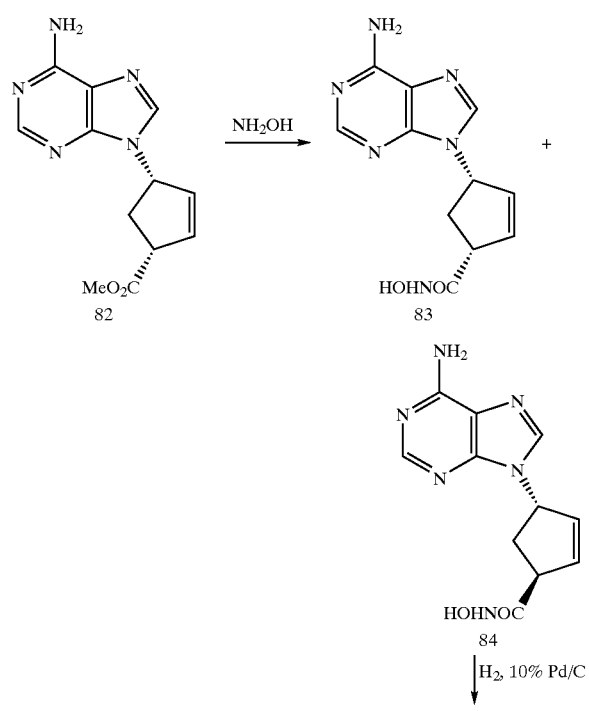

The following general procedures and particular non-limiting examples refer to preparation of compounds in Schemes I–X and are provided to better illustrate the present invention.

All of the cited patents and publications are incorporated herein by reference. The following specific examples are provided to better assist the reader in the various aspects of practicing the present invention. As these specific examples are merely illustrative, nothing in the following descriptions should be construed as limiting the invention in any way.

EXAMPLES

General Procedure A—Adenine Alkylations

Adenine (1.18 mmole) was combined with an alkyl bromide (3.54 mmoles), $K_2CO_3$ (5.91 mmoles) and DMF (5.00 mL). The mixture was heated to 60° C. for 20 hours. After cooling to room temperature, the reaction was diluted with brine (50 mL) and washed with EtOAc (3×20 mL). The combined organic washes were dried over anhydrous $MgSO_4$, filtered and concentrated to dryness. The product was purified on silica gel (5% MeOH/CHCl$_3$).

General Procedure B—Hydroxamic Acids

KOH (3.8 M in MeOH, 0.45 mL) was added to HONH$_2$ HCl (1.6 M in MeOH, 0.67 mL) and cooled to 0° C. for 2 hours. A methyl or ethyl ester (0.15 mmoles) was dissolved in MeOH (0.31 mL) and the HONH$_2$ solution was added by filtration. After stirring for 45 minutes at room temperature, the reaction was concentrated to dryness and the residue was purified by reverse phase preparative HPLC (0–10% CH$_3$CN/30 minutes). The isolated product was desalted with MP-carbonate resin (Argonaut) in MeOH, filtered and concentrated to dryness giving the desired hydroxamic acid.

General Procedure C—Carboxylic Acids

A methyl or ethyl ester (0.53 mmoles) was dissolved in MeOH (2.40 mL) and NaOH (2.00 M in H$_2$O, 1.60 mmoles)

was added. The reaction was stirred at room temperature for 2.5 hours after which, it was acidified to pH=2 with DOWEX acid resin (50WX$_2$-100, MeOH washed). The reaction was filtered and concentrated to dryness giving the desired carboxylic acid.

General Procedure D—Rhodium Acetate

An alcohol (6.08 mmoles) was dissolved in CH$_2$Cl$_2$ (65 mL) and [Rh(OAc)2]2 (0.15 mmole) was added. Ethyl diazoacetate (13.30 mmoles) was added dropwise and the reaction was stirred at room temperature for 24 hours. After concentrating to dryness, the product was purified on silica gel (20% EtOAc/hexane).

General Procedure E—Acetate/p-nitrobenzoate Cleavage (NaOMe)

An acetate or p-nitrobenzoate (5.18 mmoles) was dissolved in anhydrous MeOH (15 mL) and catalytic NaOMe (solution in MeOH) was added. The reaction was stirred at room temperature for 24 hours after which, it was quenched with H2O (1.0 mL) and concentrated to dryness. The product was purified on silica gel (50% EtOAc/Hexane).

General Procedure F—Adenine Mitsunobu

An allylic alcohol (10.93 mmoles), triphenylphosphine (10.93 mmoles) and adenine (10.93 mmoles) were dissolved in THF (40 mL) and cooled to 0° C. Diethyl azodicarboxylate (10.93 mmoles) was added dropwise and the reaction was stirred at room temperature for 18 hours. After heating the reaction to 40° C. for an additional 4 hours, the mixture was cooled to room temperature and the solids were removed by filtration. The filtrate was concentrated to dryness and the residue was purified on silica gel (EtOAc then 5% MeOH/CHCl$_3$).

General Procedure G—Olefin Hydrogenation (also Azide Reduction)

An olefin (100 mg) and 10% Pd/C (25 mg) were placed under Argon and MeOH (10 mL) was added. The mixture was degassed under vacuum and stirred under H$_2$ (1 atm) for 20 hours. The reaction was filtered and concentrated giving the desired product.

General Procedure H—TBDMS Protection

An alcohol (72.24 mmoles) was dissolved in THF (200 mL) and imidazole (108.36 mmoles) was added followed by TBDMS-Cl (90.30 mmoles). The reaction was stirred at room temperature for 24 hours after which, the solids were removed by filtration and the filtrate was concentrated to dryness. The residue was dissolved in EtOAc (300 HL) and washed with HCl (1N, 3×50 mL), saturated NaHCO$_3$ (3×50 mL) and brine (50 mL). The organic phase was dried over anhydrous MgSO$_4$, filtered and concentrated and the residue was used with no further purification.

General Procedure I—TBDMS Cleavage (AcOHfTHF/Water)

A TBDMS ether (4.52 mmoles) was combined with THF (1 mL), H$_2$O (1 mL) and acetic acid (3 mL). The reaction was stirred at room temperature for 6 hours after which, it was azeotroped with benzene (3×15 mL). The residue was dried under vacuum and purified on silica gel (25% EtOAc/Hexane).

General Procedure J—p-nitrobenzoic Acid Mitsunobu

An allylic alcohol (60.70 mmoles), p-nitrobenzoic acid (242.81 mmoles) and triphenylphospine (242.81 mmoles) were combined with THF (200 mL) and cooled to 0° C. under argon. Diethylazodicarboxylate (242.81 mmoles) was added dropwise and the reaction was stirred at room temperature for 15 hours and 40° C. for an additional 3 hours. After cooling to room temperature, the reaction was concentrated to dryness and the residue was diluted with EtOAc (200 mL). The resulting solution was washed with HCl (1N, 3×50 mL), brine (50 mL), saturated NaHOC$_3$ (3×50 mL) and brine (50 mL). After drying over anhydrous MgSO$_4$, the organics were filtered, concentrated and stirred with Et$_2$O (150 mL) for 18 hours. The resulting solids were removed by filtration and the filtrate was concentrated to dryness. The isolated residue was used without further purification.

General Procedure K—TBDMS Cleavage (TBAF)

A TBDMS ether (69.58 mmoles) was dissolved in THF (500 mL) and tetrabutylammonium fluoride (1M in THF, 104 mL) was added. The reaction was stirred at room temperature for 2 hours and concentrated to dryness. The residue was filtered through silica gel (EtOAc) and again concentrated to dryness. Final purification was achieved on silica gel (10% then 25% then 50% EtOAc/Hexane).

General Procedure L—Allyl Chloride

An allylic alcohol (46.17 mmoles) was dissolved in CH$_2$Cl$_2$ and diisopropylethyl-amine (69.25 mmoles) was added. The resulting solution was cooled to 0° C. under argon and methanesulfonyl chloride (57.71 mmoles) was added. After stirring at 0° C. for 3 hours, the reaction was diluted with EtOAc (600 mL). The mixture was then washed with HCl (1N, 3×50 mL), saturated NaHCO$_3$ (3×50 mL) and brine (50 mL). The organics were dried over anhydrous MgSO$_4$, filtered and concentrated and the residue was purified on silica gel (5% EtOAc/Hexane).

General Procedure M—Malonate Coupling

NaH (60%, 149.03 mmoles) was suspended in anhydrous THF (400 mL) and cooled to 0° C. under argon. Dimethylmalonate (149.03 mmoles) was added dropwise over 30 minutes and the reaction was allowed to warm to room temperature. An allyl chloride (29.81 mmoles) was dissolved in anhydrous THF (100 mL) and added to the malonate solution via cannula. After heating to 75° C. for 19 hours, the reaction was cooled, concentrated to a volume of 150 mL and diluted with 50% EtOAc/Hexane (300 mL). The resulting solution was washed with saturated NH$_4$Cl (3×50 mL) and brine (2×50 mL). Following concentration, the organics were partitioned between hexane (150 mL) and H$_2$O (150 mL). The hexane layer was further washed with H$_2$O (2×50 mL), dried over anhydrous MgSO$_4$, filtered and concentrated. The residue was purified on silica gel (5% EtOAc/Hexane).

General Procedure N—Decarboxylation (LiI)

A substituted malonate (31.93 mmoles) was combined with LiI (191.58 mmoles) and dissolved in DMF (260 mL). The mixture was degassed under vacuum, placed under argon and heated to 130° C. for 17 hours. After cooling to room temperature, the reaction was diluted with 25% EtOAc/Hexane (1500 mL) and washed with H$_2$O (3×300 mL) and brine (100 mL). The organic phase was dried over anhydrous MgSO$_4$, filtered and concentrated. The resulting residue was purified on silica gel (5% EtOAc/Hexane).

General Procedure O—Tritylation

An allylic alcohol (9.39 mmoles), trityl chloride (46.96 mmoles) and DMAP (56.36 mmoles) were combined and dissolved in DMF (30 mL). After heating to 100° C. for 20 hours, the reaction was cooled to room temperature and diluted with H20 (200 mL). The aqueous mixture was washed with 50% EtOAc/Hexane (200 mL) and the organics were sequentially washed with HCl (1N, 3×25 mL), saturated NaHCO$_3$ (3×25 mL) and brine (25 mL). The organics were dried over MgSO$_4$, filtered, concentrated to dryness and used without further purification.

General Procedure P—Trityl Cleavage (TsOH)

A trityl ether (15.75 mmoles) was dissolved in MeOH (100 mL) and p-toluene-sulfonic acid (0.79 mmoles) was added. After stirring at room temperature for 1.25 hours, the reaction was quenched with saturated NaHCO₃ (100 mL). The resulting mixture was washed with EtOAc (3×100 mL) and the combined organic extracts were washed with brine (50 mL). After drying over anhydrous MgSO₄, the product was purified on silica gel (25% then 50% EtOAc/Hexane).

General Procedure O—Methyl Ester Formation (MeOH, Ac—Cl)

Acetyl chloride (9.00 mmoles) was slowly added to MeOH (35.00 mL) and cooled to 0° C. A carboxylic acid (7.87 mmoles) was added and the resulting mixture was stirred at room temperature for 4 hours. Concentration of the reaction mixture provided the desired product requiring no further purification.

General Procedure R—Coupling with Pyrimidine

An amine hydrochloride (7.97 mmoles) was combined with dichloronitro-pyrimidine (11.95 mmoles) and EtOH (80 mL). Triethylamine (23.90 mmoles) was added and the reaction was stirred at room temperature for 3.5 hours. Following dilution with EtOAc (320 mL), the mixture was sequentially washed with HCl (1N, 3×50 mL), saturated NaHCO₃ (3×30 mL) and brine (30 mL). The organics were dried over anhydrous MgSO₄, filtered and concentrated. The isolated residue was used with no further purification.

General Procedure S—Nitro Group Reduction (SnCl₂)

A nitropyrimidine (9.36 mmoles) was dissolved in EtOH (75 mL) and SnCl₂ (28.09 mmoles) was added. The reaction was heated to reflux for 50 minutes and cooled to room temperature. Following quenching with saturated NaHCO₃ (300 mL), the reaction was washed with EtOAc (3×75 mL). The organic extracts were washed with brine (2×75 mL), dried over anhydrous MgSO₄, filtered and concentrated. No further purification was required.

General Procedure T—Purine Formation (Orthoformate, Ms—OH)

A diaminopyrimidine (9.36 mmoles) was dissolved in trimethylorthoformate (25 mL) and methanesulfonic acid (0.22 mL) was added. The reaction was stirred at room temperature for 4.5 hours and diluted with EtOAc (150 mL). The resulting mixture was washed with saturated NaHCO₃ (3×25 mL) and brine (25 mL). The organic phase was dried over anhydrous MgSO₄, filtered and concentrated. The product was purified on silica gel (50% EtOAc/Hexane).

General Procedure U—Azidopurine

A chloropurine (3.02 mmoles), sodium azide (9.06 mmoles), EtOH (13 mL) and H₂O (6.5 mL) were combined and heated to 50° C. for 20 hours. After stirring for an additional 17 hours at room temperature, the reaction was concentrated to dryness. The residue was diluted with H₂O (20 mL) and the resulting solids were filtered, washed with H₂O and dried in a dessicator. No further purification was required.

General Procedure V—Azide Reduction (SnCl₂)

An azidopurine (0.42 mmoles) was dissolved in EtOH (3.25 mL) and SnCl₂ (1.27 mmoles) was added. The reaction was heated to reflux for 20 minutes and cooled to room temperature. Following quenching with saturated NaHCO₃ (15 mL), the reaction was washed with EtOAc (3×15 mL). The organic extracts were dried over anhydrous MgSO4, filtered and concentrated. No further purification was required.

HPLC Methods

A 10%–90% CH₃CN/10 minutes
B 0%–90% CH₃CN/10 minutes
C 5%–85% CH₃CN/9 minutes

Methyl-3-(9-adenenyl)-propionoate (3a).

Compound 3a was prepared by coupling adenine with methylbromopropionate according to general procedure A. Yield=7%. TLC: $R_f$=0.17 (5% MeOH/CHCl₃). ¹H NMR (400 MHz, DMSO): δ3.10 (t, 2H), 3.70 (s, 3H), 4.50 (t, 2H), 7.30 (s, 2H), 8.20 (s, 1H), 8.23 (s, 1H).

Ethyl-4-(9-adenenyl)-butyrate (3b).

Compound 3b was prepared by coupling adenine with ethylbromobutyrate according to general procedure A. Yield=60%. TLC: $R_f$=0.15 (5% MeOH/CHCl₃). ¹H NMR (400 MHz, DMSO): δ1.25 (t, 3H), 2.15 (m, 2H), 2.40 (t, 2H), 4.10 (q, 2H), 4.30 (t, 2H), 7.30 (s, 2H), 8.23 (s, 1H), 8.25 (s, 1H).

Methyl-5-(9-adenenyl)-pentanoate (3c).

Compound 3c was prepared by coupling adenine with methylbromopentanoate according to general procedure A. Yield=40%. TLC: $R_f$=0.26 (5% MeOH/CHCl₃). Purity: >95% (HPLC method A). ¹H NMR (400 MHz, DMSO): δ1.58 (m, 2H), 1.95 (m, 2H), 2.45 (t, 2H), 3.65 (s, 3H), 4.25 (t, 2H), 7.30 (s, 2H), 8.23 (s, 1H), 8.25 (s, 1H).

Ethyl-6-(9-adenenyl)-hexanoate (3d).

Compound 3d was prepared by coupling adenine with ethylbromohexanoate according to general procedure A. Yield=55%. TLC: $R_f$=0.22 (5% MeOH/CHCl₃). Purity: >90% (HPLC method A). ¹H NMR (400 MHz, DMSO): δ1.25 (t, 3H), 1.35 (m, 2H), 1.65 (m, 2H), 1.90 (m, 2H), 2.35 (t, 2H), 4.10 (q, 2H), 4.25 (t, 2H), 8.23 (s, 1H), 8.25 (s, 1H).

Ethyl-7-(9-adenenyl)-heptanoate (3e).

Compound 3e was prepared by coupling adenine with ethylbromoheptanoate according to general procedure A. Yield=39%. TLC: $R_f$=0.25 (5% MeOH/CHCl₃). Purity: >95% (HPLC method A). ¹H NMR (400 MHz, DMSO): δ1.25 (t, 3H), 1.35 (m, 4H), 1.60 (m, 2H), 1.90 (m, 2H), 2.35 (t, 2H), 4.15 (q, 2H), 4.25 (t, 2H), 7.30 (s, 2H), 8.24 (s, 1H), 8.25 (s, 1H).

N-Hydroxy-3-(9-adenenyl)-propionamide (4a).

Compound 4a was prepared by subjecting compound 3a to general procedure B. Yield=60%. TLC: $R_f$=0.17 (CHCl₃/MeOH/H₂O 150/45/5). Purity: >95% (HPLC method C). ¹H NMR (400 MHz, DMSO): δ2.70 (t, 2H), 4.45 (t, 2H), 7.30 (s, 2H), 8.10 (s, 1H), 8.25 (s, 1H), 8.90 (s, 1H), 10.60 (s, 1H).

N-Hydroxy-4-(9-adenenyl)-butyramide (4b).

Compound 4b was prepared by subjecting compound 3b to general procedure B. Yield=68%. TLC: $R_f$=0.19 (CHCl₃/MeOH/H₂O 150/45/5). Purity: >99% (HPLC method B). ¹H NMR (400 MHz, DMSO): δ2.05 (m, 2H), 2.15 (m, 2H), 4.25 (t, 2H), 7.30 (s, 2H), 8.25 (s, 2H), 8.85 (s, 1H), 10.50 (s, 1H).

N-Hydroxy-5-(9-adenenyl)-pentanamide (4c).

Compound 4c was prepared by subjecting compound 3c to general procedure B. Yield=74%. TLC: $R_f$=0.24 (CHCl₃/MeOH/H₂O 150/45/5). Purity: >90% (HPLC method A). ¹H NMR (400 MHz, DMSO): δ1.50 (m, 2H), 1.90 (m, 2H), 2.10 (t, 2H), 4.20 (t, 2H), 7.30 (s, 2H), 8.20 (s, 2H), 8.75 (s, 1H), 10.40 (s, 1H).

N-Hydroxy-6-(9-adenenyl)-hexanamide (4d).

Compound 4d was prepared by subjecting compound 3d to general procedure B. Yield=80%. TLC: $R_f$=0.32 (CHCl₃/MeOH/H₂O 150/45/5). Purity: >90% (HPLC method A). ¹H NMR (400 MHz, DMSO): δ1.30 (m, 2H), 1.60 (m, 2H), 1.90 (m, 2H), 2.00 (t, 2H), 4.20 (t, 2H), 7.30 (s, 2H), 8.20 (s, 2H), 8.75 (s, 1H), 10.40 (s, 1H).

N-Hydroxy-7-(9-adenenyl)-heptanamide (4e).

Compound 4e was prepared by subjecting compound 3e to general procedure B. Yield=93%. TLC: $R_f$=0.42 (CDCl₃/MeOH/H₂O 150/45/5). Purity: >90% (HPLC method A). ¹H NMR (400 MHz, DMSO): δ1.30 (m, 4H), 1.55 (m, 2H), 1.90 (m, 2H), 2.00 (t, 2H), 4.20 (t, 2H), 7.30 (s, 2H), 8.20 (s, 2H), 8.75 (s, 1H), 10.40 (s, 1H).

5-(9-Adenenyl)-pentanoic acid (5c).

Compound 5c was prepared by subjecting compound 3c to general procedure C. Yield=26%. Purity: >95% (HPLC method A). ¹H NMR (400 MHz, DMSO): δ1.50 (m, 2H), 1.90 (m, 2H), 2.35 (t, 2H), 4.20 (t, 2H), 7.30 (s, 2H), 8.21 (s, 1H), 8.22 (s, 1H), 12.2 (s, 1H).

6-(9-Adenenyl)-hexanoic acid (5d).

Compound 5d was prepared by subjecting compound 3d to general procedure C. Yield=31%. Purity: >95% (HPLC method A). ¹H NMR (400 MHz, DMSO): δ1.35 (m, 2H), 1.60 (m, 2H), 1.90 (m, 2H), 2.30 (t, 2H), 4.20 (t, 2H), 7.30 (s, 2H), 8.21 (s, 1H), 8.22 (s, 1H), 12.2 (bs, 1H).

7-(9-Adenenyl)-heptanoic acid (5e).

Compound 5e was prepared by subjecting compound 3e to general procedure C. Yield=31%. Purity: >95% (HPLC method A). ¹H NMR (400 MHz, DMSO): δ1.35 (m, 4H), 1.55 (m, 2H), 1.90 (m, 2H), 2.30 (t, 2H), 4.20 (t, 2H), 7.30 (s, 2H), 8.21 (s, 1H), 12.1 (s, 1H).

(1R, 3S)-1-Hydroxy-3-(methyl-carboxymethoxy)-4-cyclopentene (7).

(1R, 3S)-1-Acetoxy-3-hydroxy-4-cyclopentene was subjected to general procedure D. Yield=85%. TLC: $R_f$=0.33 (25% EtOAc/Hexane). ¹H NMR (400 MHz, CDCl₃): δ1.25 (t, 3H), 1.75 (m, 1H), 2.05 (s, 3H), 2.75 (m, 1H), 4.10 (s, 2H), 4.20 (q, 2H), 4.55 (m, 1H), 5.45 (m, 1H), 6.00 (d, 1H), 6.15 (d, 1H). Subsequent subjection of the product to general procedure E gave compound 7. Yield=84%. TLC: $R_f$=0.59 (EtOAc). 1H NMR (400 MHz, CDCl₃): δ1.70 (s, 2H), 2.65 (m, 1H), 3.75 (s, 3H), 4.10 (s, 2H), 4.45 (m, 1H), 4.65 (m, 1H), 6.05 (m, 2H).

(1S, 3S)-1-(9-Adenenyl)-3-(methyl-carboxymethoxy)-4-cyclopentene (8).

Compound 8 was prepared by subjecting compound 7 to general procedure F. Yield=17%. TLC: $R_f$=0.16 (5% MeOH/CHCl₃). Purity: >93% (HPLC method C). ¹H NMR (400 MHz, DMSO): δ2.45 (m, 2H), 3.80 (s, 3H), 4.35 (s, 2H), 5.10 (m, 1H), 5.85 (m, 1H), 6.25 (m, 1H), 6.45 (m, 1H), 7.35 (s, 2H), 8.15 (s, 1H), 8.25 (s, 1H)

(1S, 3S)-1-(9-Adenenyl)-3-(N-hydroxycarbamoylmethoxy)-4-cyclopentene (9).

Compound 9 was prepared by subjecting compound 8 to general procedure B. Yield=95%. TLC: $R_f$=0.33 (CHCl₃/MeOH/H₂O 150/45/5). Purity: >91% (HPLC method C). ¹H NMR (400 MHz, DMSO): δ2.45 (m, 1H), 2.55 (m, 1H), 4.05 (s, 2H), 5.05 (m, 1H), 5.90 (m, 1H), 6.30 (m, 1H), 6.50 (m, 1H), 7.95 (bs, 2H), 8.25 (s, 1H), 8.35 (s, 1H), 8.95 (s, 1H), 10.70 (s, 1H).

(1S, 3S)-1-(9-Adenenyl)-3-carboxymethoxy-4-cyclopentene (10).

Compound 10 was prepared by subjecting compound 8 to general procedure C. Yield=52%. TLC: $R_f$=0.07 (CHCl₃/MeOH/H₂O 150145/5). Purity: >99% (HPLC method C). ¹H NMR (400 MHz, DMSO): δ2.45 (m, 2H), 4.10 (s, 2H), 5.10 (m, 1H), 5.85 (m, 1H), 6.25 (m, 1H), 6.45 (m, 1H), 7.35 (s, 2H), 8.15 (s, 1H), 8.25 (s, 1H)

(1R, 3R)-1-(9-Adenenyl)-3-(methyl-carboxymethoxy)cyclopentane (11).

Compound 11 was prepared by subjecting compound 8 to general procedure G. Yield=85%. TLC: $R_f$=0.33 (CHCl₃/MeOH/H₂O 150/45/5). Purity: >95% (HPLC method C). ¹H NMR (400 MHz, DMSO): δ1.90 (m, 1H), 2.10 (m, 1H), 2.35 (m, 4H), 3.80 (s, 3H), 4.25 (s, 2H), 4.35 (m, 1H), 5.10 (m, 1H), 7.30 (s, 2H), 8.20 (s, 1H), 8.35 (s, 1H).

(1R, 3R)-1-(9-Adenenyl)-3-(N-hydroxycarbamoylmethoxy) cyclopentane (12).

Compound 12 was prepared by subjecting compound 11 to general procedure B. Yield=99%. TLC: $R_f$=0.22 (5% MeOH/CHCl₃). Purity: >99% (HPLC method C). ¹H NMR (400 MHz, DMSO): δ1.90 (m, 1H), 2.10 (m, 1H), 2.35 (m, 4H), 3.95 (s, 2H), 4.30 (m, 1H), 5.10 (m, 1H), 7.35 (s, 2H), 8.20 (s, 1H), 8.35 (s, 1H), 8.95 (s, 1H), 10.65 (s, 1H).

(1R, 3R)-1-(9-Adenenyl)-3-carboxymethoxycyclopentane (13).

Compound 13 was prepared by subjecting compound 11 to general procedure C. Yield=65%. TLC: $R_f$=0.07 (CHCl₃/MeOH/H₂O 150/45/5). Purity: >99% (HPLC method C). ¹H NMR (400 MHz, DMSO): δ1.90 (m, 1H), 2.10 (m, 1H), 2.35 (m, 4H), 4.15 (s, 2H), 4.35 (m, 1H), 5.10 (m, 1H), 7.30 (s, 2H), 8.25 (s, 1H), 8.35 (s, 1H).

(1R, 3S)-1-Hydroxy-3-(tert-Butyl-dimethylsiloxy)-4-cyclopentene (14).

(1R, 3S)-1-Acetoxy-3-hydroxy-4-cyclopentene to general procedure H. Yield=100%. TLC: $R_f$=0.48 (10% EtOAc/Hexane). ¹H NMR (400 MHz, CDCl₃): δ0.05 (s, 6H), 0.90 (s, 9H), 1.55 (m, 1H), 2.00 (s, 3H), 2.80 (m, 1H), 4.70 (m, 1H), 5.45 (m, 1), 5.85 (m, 1H), 5.95 (m, 1H). Subsequent subjection of the product to general procedure E gave compound 14. Yield=90%. TLC: $R_f$=0.43 (25% EtOAc/Hexane). ¹H NMR (400 MHz, CDCl₃): δ0.05 (s, 6H), 0.90 (s, 9H), 1.50 (m, 1H), 2.65 (m, 1H), 4.55 (m, 1H), 4.65 (m, 1H), 5.85 (m, 1H), 5.95 (m, 1H).

(1S, 3R)-1-Hydroxy-3-(ethyl-carboxymethoxy)-4-cyclopentene (15).

Compound 14 was subjected to general procedure D. Yield=77%. TLC: $R_f$=0.29 (10% EtOAc/Hexane). ¹H NMR (400 MHz, CDCl₃): δ0.05 (s, 6H), 0.90 (s, 9H), 1.25 (t, 3H), 1.60 (m, 1H), 2.65 (m, 1H), 4.10 (s, 2H), 4.20 (q, 2H), 4.55 (m, 1H), 4.65 (m, 1H), 5.95 (m, 2H). Subsequent subjection of the product to general procedure I gave compound 15. Yield=79%. TLC: $R_f$=0.65 (EtOAc). ¹H NMR (400 MHz, CDCl₃): δ1.25 (t, 3H), 1.65 (m, 1H), 1.75 (s, 1H), 2.65 (m, 1H), 4.10 (s, 2H), 4.20 (q, 2H), 4.45 (m, 1H), 4.65 (m, 1H), 6.05 (m, 2H).

(1R, 3R)-1-(9-Adenenyl)-3-(ethyl-carboxymethoxy)-4-cyclopentene (16).

Compound 16 was prepared by subjecting compound 15 to general procedure F. Yield=21%. TLC: $R_f$=0.18 (5% MeOH/CHCl₃). Purity: >95% (HPLC method C). ¹H NMR (400 MHz, DMSO): δ1.35 (t, 3H), 2.45 (m, 2H), 4.25 (q, 2H), 4.35 (s, 2H), 5.10 (m, 1H), 5.85 (m, 1H), 6.25 (m, 1H), 6.45 (m, 1H), 7.35 (s, 2H), 8.15 (s, 1H), 8.25 (s, 1H).

(1R, 3R)-1-(9-Adenenyl)-3-(N-hydroxycarbamoylmethoxy)-4-cyclopentene (17).

Compound 17 was prepared by subjecting compound 16 to general procedure B. Yield=88%. TLC: $R_f$=0.33 (CHCl₃/MeOH/H₂O 150/45/5). Purity: >95% (HPLC method C). ¹H NMR (400 MHz, DMSO): δ2.45 (m, 1H), 2.55 (m, 1H), 4.05 (s, 2H), 5.05 (m, 1H), 5.90 (m, 1H), 6.30 (m, 1H), 6.50 (m, 1H), 7.30 (bs, 2H), 8.10 (s, 1H), 8.20 (s, 1H), 8.95 (s, 1H), 10.70 (s, 1H).

(1R, 3R)-1-(9-Adenenyl)-3-carboxymethoxy-4-cyclopentene (18).

Compound 18 was prepared by subjecting compound 16 to general procedure C. Yield=70%. TLC: $R_f$=0.07 (CHCl₃/MeOH/H₂O 150/45/5). Purity: >95% (HPLC method C). ¹H NMR (400 MHz, DMSO): δ2.45 (m, 2H), 4.10 (s, 2H), 5.10 (m, 1H), 5.85 (m, 1H), 6.25 (m, 1H), 6.45 (m, 1H), 7.35 (s, 2H), 8.15 (s, 1H), 8.25 (s, 1H).

(1S, 3S)-1-(9-Adenenyl)-3-(ethyl-carboxymethoxy) cyclopentane (19).

Compound 19 was prepared by subjecting compound 16 to general procedure G. Yield=94%. TLC: $R_f$=0.23 (CHCl₃/MeOH/H2O 150/45/5). Purity: >95% (HPLC method C). ¹H NMR (400 MHz, DMSO): δ1.35 (t, 3H), 1.90 (m, 1H), 2.10 (m, 1H), 2.35 (m, 4H), 4.25 (s, 2H), 4.28 (q, 2H), 4.35 (m, 1H), 5.10 (m, 1H), 7.30 (s, 2H) 8.20 (s, 1H), 8.35 (s, 1H).

(1S, 3S)-1-(9-Adenenyl)-3-(N-hydroxycarbamoylmethoxy) cyclopentane (20).

Compound 20 was prepared by subjecting compound 19 to general procedure B. Yield=90%. TLC: R$_f$=0.36 (CHCl$_3$/MeOH/H$_2$O 150/45/5). Purity: >95% (HPLC method C). $^1$H NMR (400 MHz, DMSO): δ1.90 (m, 1H), 2.10 (m, 1H), 2.35 (m, 4H), 3.95 (s, 2H), 4.30 (m, 1H), 5.10 (m, 1H), 7.35 (s, 2H), 8.20 (s, 1H), 8.35 (s, 1H), 8.95 (s, 1H), 10.65 (s, 1H).

(1S, 3S)-1-(9-Adenenyl)-3-carboxymethoxycyclopentane (21).

Compound 21 was prepared by subjecting compound 19 to general procedure C. Yield=100%. TLC: R$_f$=0.07 (CHCl$_3$/MeOH/H$_2$O 150/45/5). Purity: >95% (HPLC method C). $^1$H NMR (400 MHz, DMSO): δ1.90 (m, 1H), 2.10 (m, 1H), 2.35 (m, 4H), 4.15 (s, 2H), 4.35 (m, 1H), 5.10 (m, 1H), 7.30 (s, 2H), 8.25 (s, 1H), 8.35 (s, 1H).

(1R, 3R)-1-(tert-Butyl-dimethylsiloxy)-3-hydroxy-4-cyclopentene (22).

Compound 14 was subjected to general procedure J. Yield=81%. TLC: R$_f$=0.50 (10% EtOAc/Hexane). $^1$H NMR (400 MHz, CDCl$_3$): δ0.05 (s, 6H), 0.90 (s, 9H), 2.20 (m, 1H), 2.30 (m, 1H), 5.10 (s, 1H), 6.05 (m, 2H), 6.10 (m, 1H), 8.20 (d, 2H), 8.20 (d, 2H). Subsequent subjection of the product to general procedure E gave compound 22. Yield=85%. TLC: R$_f$=0.33 (25% EtOAc/Hexane). $^1$H NMR (400 MHz, CDCl$_3$): δ0.05 (s, 6H), 0.90 (s, 9H), 2.05 (m, 2H), 5.00 (m, 1H), 5.05 (m, 1H), 5.95 (m, 2H).

(1S, 3S)-1-Hydroxy-3-(ethyl-carboxymethoxy)-4-cyclopentene (23).

Compound 22 was subjected to general procedure D. Yield=71%. TLC: R$_f$=0.33 (10% EtOAc/Hexane). $^1$H NMR (400 MHz, CDCl$_3$): δ0.05 (s, 6H), 0.90 (s, 9H), 1.30 (t, 3H), 1.90 (m, 1H), 2.20 (m, 1H), 4.05 (s, 2H), 4.20 (q, 2H), 4.75 (m, 1H), 5.05 (m, 1H), 6.00 (m, 2H). Subsequent subjection of the product to general procedure K gave compound 23. Yield=91%. TLC: R$_f$=0.25 (50% EtOAc/Hexane). $^1$H NMR (400 MHz, CDCl$_3$): δ1.25 (t, 3H), 2.00 (m, 1H), 2.25 (m, 1H), 4.05 (s, 2H), 4.20 (q, 2H), 4.80 (m, 1H), 5.05 (m, 1H), 6.05 (m, 2H).

(1R, 3S)-1-(9-Adenenyl)-3-(ethyl-carboxymethoxy)-4-cyclopentene (24).

Compound 24 was prepared by subjecting compound 23 to general procedure F. Yield=13%. TLC: R$_f$=0.21 (5% MeOH/CHCl$_3$). Purity: >95% (HPLC method C). $^1$H NMR (400 MHz, DMSO): δ1.30 (t, 3H), 2.05 (m, 1H), 3.00 (m, 1H), 4.25 (q, 2H), 4.35 (s, 2H), 4.80 (m, 1H), 5.60 (m, 1H), 6.30 (m, 1H), 6.45 (m, 1H), 7.35 (s, 2H), 8.15 (s, 1H), 8.25 (s, 1H).

(1R, 3S)-1-(9-Adenenyl)-3-(N-hydroxycarbamoylmethoxy)-4-cyclopentene (25).

Compound 25 was prepared by subjecting compound 24 to general procedure B. Yield=88%. TLC: R$_f$=0.32 (CHCl$_3$/MeOH/H$_2$O 150/45/5). Purity: >90% (HPLC method C). $^1$H NMR (400 MHz, DMSO): δ2.05 (m, 1H), 3.00 (m, 1H), 4.10 (s, 2H), 4.75 (m, 1H), 5.60 (m, 1H), 6.25 (m, 1H), 6.45 (m, 1H), 7.35 (s, 2H), 8.15 (s, 1H), 8.25 (s, 1H), 8.95 (s, 1H), 10.70 (s, 1H).

(1R, 3S)-1-(9-Adenenyl)-3-carboxymethoxy-4-cyclopentene (26).

Compound 26 was prepared by subjecting compound 24 to general procedure C. Yield=100%. TLC: R$_f$=0.07 (CHCl$_3$/MeOH/H$_2$O 150/45/5). Purity: >75% (HPLC method C). $^1$H NMR (400 MHz, DMSO): δ2.00 (m, 1H), 2.95 (m, 1H), 3.90 (s, 2H), 4.75 (m, 1H), 5.55 (m, 1H), 6.20 (m, 1H), 6.45 (m, 1H), 7.30 (s, 2H), 8.10 (s, 1H), 8.15 (s, 1H).

(1S, 3R)-1-(9-Adenenyl)-3-(ethyl-carboxymethoxy)cyclopentane (27).

Compound 27 was prepared by subjecting compound 24 to general procedure G. Yield=89%. TLC: R$_f$=0.18 (5% MeOH/CHCl$_3$). Purity: >95% (HPLC method C). $^1$H NMR (400 MHz, DMSO): δ1.35 (t, 3H), 1.95 (m, 1H), 2.10 (m, 1H), 2.15 (m, 2H), 2.35 (m, 1H), 2.60 (m, 1H), 4.25 (m, 5H), 5.05 (m, 1H), 7.30 (s, 2H), 8.25 (s, 1H), 8.35 (s, 1H).

(1S, 3R)-1-(9-Adenenyl)-3-(N-hydroxycarbamoylmethoxy)cyclopentane (28).

Compound 28 was prepared by subjecting compound 27 to general procedure B. Yield=86%. TLC: R$_f$=0.35 (CHCl$_3$/MeOH/H$_2$O 150/45/5). Purity: >95% (HPLC method C). $^1$H NMR (400 MHz, DMSO): δ1.90 (m, 1H), 2.10 (m, 1H), 2.20 (m, 3H), 2.60 (m, 1H), 3.95 (s, 2H), 4.20 (m, 1H), 5.00 (m, 1H), 7.30 (s, 2H), 8.20 (s, 1H), 8.35 (s, 1H), 8.95 (s, 1H), 10.65 (s, 1H).

(1S, 3R)-1-(9-Adenenyl)-3-carboxymethoxycyclopentane (29).

Compound 29 was prepared by subjecting compound 27 to general procedure C. Yield=100%. TLC: R$_f$=0.11 (CHCl$_3$/MeOH/H$_2$O 150/45/5). Purity: >90% (HPLC method C). $^1$H NMR (400 MHz, DMSO): δ1.90 (m, 1H), 2.10 (m, 1H), 2.15 (m, 2H), 2.30 (m, 1H), 2.55 (m, 1H), 4.00 (s, 2H), 4.25 (m, 1H), 5.00 (m, 1H), 7.30 (s, 2H), 8.25 (s, 1H), 8.50 (s, 1H).

(1R, 3R)-1-Hydroxy-3-(methyl-carboxymethoxy)-4-cyclopentene (30).

Compound 15 was subjected to general procedure J. Yield=89%. TLC: R$_f$=0.31 (25% EtOAc/Hexane). $^1$H NMR (400 MHz, CDCl$_3$): δ1.30 (t, 3H), 2.35 (m, 2H), 4.10 (s, 2H), 4.25 (q, 2H), 4.90 (m, 1H), 6.05 (m, 1H), 6.20 (m, 1H), 6.30 (m, 1H), 8.20 (d, 2H), 8.30 (d, 2H). Subsequent subjection of the product to general procedure E gave compound 30. Yield=91%. TLC: R$_f$=0.18 (50% EtOAc/Hexane). $^1$H NMR (400 MHz, CDCl$_3$): δ2.00 (m, 1H), 2.25 (m, 1H), 3.75 (s, 3H), 4.05 (s, 2H), 4.80 (m, 1H), 5.05 (m, 1H), 6.05 (s, 2H).

(1S, 3R)-1-(9-Adenenyl)-3-(methyl-carboxymethoxy)-4-cyclopentene (31).

Compound 31 was prepared by subjecting compound 30 to general procedure F. Yield=16%. TLC: R$_f$=0.14 (5% MeOH/CHCl$_3$). Purity: >95% (HPLC method C). $^1$H NMR (400 MHz, DMSO): δ2.05 (m, 1H), 3.00 (m, 1H), 3.75 (s, 3H), 4.35 (s, 2H), 4.80 (m, 1H), 5.60 (m, 1H), 6.30 (m, 1H), 6.45 (m, 1H), 7.35 (s, 2H), 8.15 (s, 1H), 8.25 (s, 1H).

(1S, 3R)-1-(9-Adenenyl)-3-(N-hydroxycarbamoylmethoxy)-4-cyclopentene (32).

Compound 32 was prepared by subjecting compound 31 to general procedure B. Yield=100%. TLC: R$_f$=0.32 (CHCl$_3$/MeOH/H$_2$O 150/45/5). Purity: >95% (HPLC method C). $^1$H NMR (400 MHz, DMSO): δ2.05 (m, 1H), 3.00 (m, 1H), 4.10 (s, 2H), 4.75 (m, 1H), 5.60 (m, 1H), 6.25 (m, 1H), 6.45 (m, 1H), 7.35 (s, 2H), 8.15 (s, 1H), 8.25 (s, 1H), 8.95 (s, 1H), 10.70 (s, 1H).

(1S, 3R)-1-(9-Adenenyl)-3-carboxymethoxy-4-cyclopentene (33).

Compound 33 was prepared by subjecting compound 31 to general procedure C. Yield=88%. TLC: R$_f$=0.07 (CHCl$_3$/MeOH/H$_2$O 150/45/5). Purity: >95% (HPLC method C). $^1$H NMR (400 MHz, DMSO): δ2.00 (m, 1H), 2.95 (m, 1H), 4.15 (s, 2H), 4.75 (m, 1H), 5.60 (m, 1H), 6.25 (m, 1H), 6.45 (m, 1H), 7.35 (s, 2H), 8.15 (s, 1H), 8.25 (s, 1H).

(1R, 3S)-1-(9-Adenenyl)-3-(methyl-carboxymethoxy)cyclopentane (34).

Compound 34 was prepared by subjecting compound 31 to general procedure G. Yield=95%. TLC: R$_f$=0.24 (5% MeOH/CHCl$_3$). Purity: >95% (HPLC method C). $^1$H NMR (400 MHz, DMSO): δ1.95 (m, 1H), 2.10 (m, 1H), 2.15 (m, 2H), 2.35 (m, 1H), 2.60 (m, 1H), 3.80 (s, 3H), 4.25 (m, 1H), 4.30 (s, 2H), 5.05 (m, 1H), 7.30 (s, 2H) 8.25 (s, 1H), 8.35 (s, 1H).

(1R, 3S)-1-(9-Adenenyl)-3-(N-hydroxycarbamoylmethoxy) cyclopentane (35).

Compound 35 was prepared by subjecting compound 34 to general procedure B. Yield=87%. TLC: $R_f$=0.34 (CHCl$_3$/MeOH/H$_2$O 150/45/5). Purity: >90% (HPLC method C). $^1$H NMR (400 MHz, DMSO): δ1.90 (m, 1H), 2.10 (m, 1H), 2.20 (m, 3H), 2.60 (m, 1H), 3.95 (s, 2H), 4.20 (m, 1H), 5.00 (m, 1H), 7.30 (s, 2H), 8.20 (s, 1H), 8.35 (s, 1H), 9.00 (s, 1H), 10.70 (s, 1H).

(1R, 3S)-1-(9-Adenenyl)-3-carboxymethoxycyclopentane (36).

Compound 36 was prepared by subjecting compound 34 to general procedure C. Yield=95%. TLC: $R_f$=0.08 (CHCl$_3$/MeOH/H$_2$O 150/45/5). Purity: >85% (HPLC method C). $^1$H NMR (400 MHz, DMSO): δ1.90 (m, 1H), 2.10 (m, 1H), 2.15 (m, 2H), 2.30 (m, 1H), 2.55 (m, 1H), 3.90 (s, 2H), 4.25 (m, 1H), 5.00 (m, 1H), 7.30 (s, 2H), 8.25 (s, 1H), 8.60 (s, 1H).

(1S, 3R)-1-Hydroxy-3-triphenylmethoxy-4-cyclopentene (37).

Compound 14 was subjected to general procedure O. TLC: $R_f$=0.27 (Hexane). $^1$H NMR (400 MHz, CDCl$_3$): δ0.00 (s, 6H), 1.85 (s, 9H), 1.55 (m, 1H), 2.15 (m, 1H), 4.35 (m, 2H), 4.95 (m, 1H), 5.60 (m, 1H), 7.20 (m, 3H), 7,25 (m, 6H), 7.50 (d, 6H). Subsequent subjection of the product to general procedure K gave compound 37. Yield=87% (2 steps). TLC: $R_f$=0.32 (25% EtOAc/Hexane). 1H NMR (400 MHz, CDCl$_3$): δ1.40 (m, 1H), 2.20 (m, 1H), 4.35 (m, 1H), 4.45 (m, 1H), 5.15 (m, 1H), 5.75 (m, 1H), 7.20 (m, 3H), 7,25 (t, 6H), 7.50 (d, 6H).

(1R, 3R)-1-Chloro-3-triphenylmethoxy-4-cyclopentene (38).

Compound 38 was prepared by subjecting compound 37 to general procedure L. Yield=84%. TLC: $R_f$=0.61 (10% EtOAc/Hexane). $^1$H NMR (400 MHz, CDCl$_3$): δ2.00 (m, 1H), 2.15 (m, 1H), 4.95 (m, 2H), 5.15 (m, 1H), 5.80 (m, 1H), 7.20 (m, 3H) 7.25 (t, 6H), 7.50 (d, 6H).

(1S, 3R)-1-(2-Dimethylmalonyl)-3-triphenylmethoxy-4-cyclopentene (39).

Compound 39 was prepared by subjecting compound 38 to general procedure M. Yield=72%. TLC: $R_f$=0.27 (10% EtOAc/Hexane). $^1$H NMR (400 MHz, CDCl$_3$): δ1.35 (m, 1H), 2.05 (m, 1H), 3.00 (m, 1H), 3.30 (d, 1H), 3.70 (s, 6H), 4.60 (m, 1H) 4.90 (m, 1H), 5.60 (m, 1H), 7.20 (m, 3H), 7.25 (t, 6H), 7.45 (d, 6H).

(1R, 3R)-1-Hydroxy-3-(methyl-carboxymethyl)-4-cyclopentene (40).

Compound 39 was subjected to general procedure N. Yield=80%. TLC: $R_f$=0.45 (10% EtOAc/Hexane). $^1$H NMR (400 MHz, CDCl$_3$): δ1.30 (m, 1H), 2.10 (m, 1H), 2.35 (m, 1H), 2.45 (m, 1H), 2.75 (m, 1H), 3.65 (s, 3H), 4.60 (m, 1H), 4.85 (m, 1H), 5.60 (m, 1H), 7.20 (m, 3H), 7.25 (t, 6H), 7.45 (d, 6H). Subsequent subjection of the product to general procedure P gave compound 40. Yield=39%. TLC: $R_f$=0.38 (50% EtOAc/Hexane). $^1$H NMR (400 MHz, CDCl$_3$): δ1.40 (m, 1H), 2.45 (m, 2H), 2.55 (m, 1H), 2.95 (m, 1H), 3.65 (s, 3H), 4.80 (m, 1H), 5.85 (m, 2H).

(1S, 3R)-1-(9-Adenenyl)-3-(methyl-carboxymethyl)-4-cyclopentene (41).

Compound 41 was prepared by subjecting compound 40 to general procedure F. Yield=9%. TLC: $R_f$=0.22 (5% MeOH/CHCl$_3$). Purity: >85% (HPLC method C). $^1$H NMR (400 MHz, DMSO): δ2.30 (m, 2H), 2.60 (m, 2H), 3.50 (m, 1H), 3.75 (s, 3H), 5.75 (m, 1H), 6.05 (m, 1H), 6.30 (m, 1H), 7.40 (s, 2H), 8.10 (s, 1H), 8.25 (s, 1H).

(1S, 3R)-1-(9-Adenenyl)-3-(N-hydroxycarbamoylmethyl)-4-cyclopentene (42).

Compound 42 was prepared by subjecting compound 41 to general procedure B. Yield=37%. TLC: $R_f$=0.40 (CHCl$_3$/MeOH/H$_2$O 150/45/5). Purity: >97% (HPLC method C). 1H NMR (400 MHz, DMSO): δ2.20 (m, 2H), 2.30 (m, 2H), 5.70 (m, 1H), 6.00 (m, 1H), 6.30 (m, 1H), 7.30 (s, 2H), 8.10 (s, 1H), 8.25 (s, 1H), 8.90 (s, 1H), 10.55 (s, 1H).

(1S, 3R)-1-(9-Adenenyl)-3-carboxymethyl-4-cyclopentene (43).

Compound 43 was prepared by subjecting compound 41 to general procedure C. Yield=97%. TLC: $R_f$=0.42 (CHCl$_3$/MeOH/H$_2$O 150/455). Purity: >86% (HPLC method C). $^1$H NMR (400 MHz, DMSO): δ2.20–2.40 (m, 4H), 3.45 (m, 1H), 5.70 (m, 1H), 6.00 (m, 1H), 6.30 (m, 1H), 7.30 (s, 2H), 8.10 (s, 1H), 8.20 (s, 1H).

(1R, 3R)-1-(9-Adenenyl)-3-(methyl-carboxymethyl) cyclopentane (44).

Compound 44 was prepared by subjecting compound 41 to general procedure G. Yield=95%. TLC: $R_f$=0.21 (CHCl$_3$/MeOH/H$_2$O 150/45/5). Purity: >86% (HPLC method C). 1H NMR (400 MHz, DMSO): δ1.45 (m, 1H), 1.95 (m, 1H), 2.20 (m, 2H), 2.30 (m, 2H), 2.55 (d, 2H), 2.75 (m, 1H), 3.75 (s, 3H), 5.05 (m, 1H), 7.35 (s, 2H), 8.25 (s, 1H), 8.35 (s, 1H).

(1R, 3R)-1-(9-Adenenyl)-3-(N-hydroxycarbamoylmethyl) cyclopentane (45).

Compound 45 was prepared by subjecting compound 44 to general procedure B. Yield=39%. TLC: $R_f$=0.34 (CHCl$_3$/MeOH/H$_2$O 150/455). Purity: >99% (HPLC method C). $^1$H NMR (400 MHz, DMSO): δ1.45 (m, 1H), 1.95 (m, 1H), 2.15 (d, 2H), 2.20 (m, 3H), 2.35 (m, 1H), 2.70 (m, 1H), 5.05 (m, 1H), 7.30 (s, 2H), 8.25 (s, 1H) 8.35 (s, 1H), 8.85 (s, 1H), 10.50 (s, 1H).

(1R, 3R)-1-(9-Adenenyl)-3-carboxymethylcyclopentane (46).

Compound 46 was prepared by subjecting compound 44 to general procedure C. Yield=83%. TLC: $R_f$=0.38 (CHCl$_3$/MeOH/H$_2$O 150/45/5). Purity: >80% (HPLC method C). $^1$H NMR (400 MHz, DMSO): δ1.45 (m, 1H), 1.95 (m, 1H), 2.15–2.40 (m, 4H), 2.45 (d, 2H), 2.70 (m, 1H), 5.05 (m, 1H), 7.30 (s, 2H), 8.25 (s, 1H), 8.35 (s, 1H).

(1S, 3S)-1-Chloro-3-(tert-Butyl-dimethylsiloxy)-4-cyclopentene (47).

Compound 47 was prepared by subjecting compound 14 to general procedure L. Yield=79%. TLC: $R_f$=0.80 (10% EtOAc/Hexane). $^1$H NMR (400 MHz, CDCl$_3$): δ0.10 (s, 6H), 0.90 (s, 9H), 2.15 (m, 1H), 2.50 (m, 1H), 5.05 (m, 1H), 5.15 (m, 1H), 5.95 (m, 2H).

(1R, 3S)-1-(2-Dimethylmalonyl)-3-(tert-Butyl-dimethylsiloxy)-4-cyclopentene (48).

Compound 48 was prepared by subjecting compound 47 to general procedure M. Yield=74%. TLC: $R_f$=0.32 (10% EtOAc/Hexane). $^1$H NMR (400 MHz, CDCl$_3$): δ0.10 (s, 6H), 0.90 (s, 9H), 1.40 (m, 1H), 2.40 (m, 1H), 3.20 (m, 1H), 3.35 (m, 1H) 3.75 (s, 6), 4.80 (m, 1H), 5.80 (m, 2H).

(1S, 3S)-1-Hydroxy-3-(methyl-carboxymethyl)-4-cyclopentene (49)

Compound 48 was subjected to general procedure N. Yield=75%. TLC: $R_f$=0.57 (10% EtOAc/Hexane). $^1$H NMR (400 MHz, CDCl$_3$): δ0.05 (s, 6H), 0.90 (s, 9H), 1.30 (m, 1H), 2.35 (m, 1H), 2.45 (m, 2H), 2.90 (m, 1H), 3.65 (s, 3H), 4.80 (m, 1H), 5.75 (m, 1H), 5.80 (m, 1H). Subsequent subjection of the product to general procedure I gave compound 49. Yield=61%. TLC: $R_f$=0.39 (50% EtOAc/Hexane). $^1$H NMR (400 MHz, CDCl$_3$): δ1.40 (m, 1H), 2.25 (m, 2H), 2.35 (m, 1H), 2.95 (m, 1H), 3.65 (s, 3H), 4.80 (m, 1H), 5.85 (m, 2H).

(1R, 3S)-1-(9-Adenenyl)-3-(methyl-carboxymethyl)-4-cyclopentene (50).

Compound 50 was prepared by subjecting compound 49 to general procedure F. Yield=10%. TLC: $R_f$=0.14 (5%

MeOH/CHCl₃). Purity: >85% (HPLC method C). ¹H NMR (400 MHz, DMSO): δ2.30 (m, 2H), 2.60 (m, 2H), 3.75 (s, 3H), 5.75 (m, 1H), 6.05 (m, 1H), 6.30 (m, 1H), 7.30 (s, 2H), 8.10 (s, 1H), 8.25 (s, 1H).

(1R, 3S)-1-(9-Adenenyl)-3-(N-hydroxycarbamoylmethyl)-4-cyclopentene (51).

Compound 51 was prepared by subjecting compound 50 to general procedure B. Yield=63%. TLC: $R_f$=0.40 (CHCl₃/MeOH/H₂O 150/45/5). Purity: >90% (HPLC method C). 1H NMR (400 MHz, DMSO): δ2.20 (m, 2H), 2.30 (m, 2H), 5.70 (m, 1H), 6.00 (m, 1H), 6.30 (m, 1H), 7.30 (s, 2H), 8.10 (s, 1H), 8.25 (s, 1H), 9.10 (s, 1H), 10.60 (s, 1H).

(1R, 3S)-1-(9-Adenenyl)-3-carboxymethyl-4-cyclopentene (52).

Compound 52 was prepared by subjecting compound 50 to general procedure C. Yield=100%. TLC: $R_f$=0.31 (CHCl₃/MeOH/H₂O 150/455). Purity: >85% (HPLC method C). ¹H NMR (400 MHz, DMSO): δ2.20–2.40 (m, 4H), 4.15 (m, 1H), 5.70 (m, 1H), 5.95 (m, 1H), 6.30 (m, 1H), 7.30 (s, 2H), 8.10 (s, 1H), 8.20 (s, 1H).

(1S, 3S)-1-(9-Adenenyl)-3-(methyl-carboxymethyl)cyclopentane (53).

Compound 53 was prepared by subjecting compound 50 to general procedure G. Yield=93%. TLC: $R_f$=0.22 (CHCl₃/MeOH/H₂O 150/45/5). Purity: >93% (HPLC method C). ¹H NMR (400 MHz, DMSO): δ1.45 (m, 1H), 1.95 (m, 1H), 2.20 (m, 2H), 2.30 (m, 2H), 2.55 (d, 2H), 2.75 (m, 1H), 3.75 (s, 3H), 5.05 (m, 1H), 7.35 (s, 2H), 8.25 (s, 1H), 8.35 (s, 1H).

(1S, 3S)-1-(9-Adenenyl)-3-(N-hydroxycarbamoylmethyl)cyclopentane (54).

Compound 54 was prepared by subjecting compound 53 to general procedure B. Yield=34%. TLC: $R_f$=0.39 (CHCl₃/MeOH/H₂O 150/45/5). Purity: >85% (HPLC method C). 1H NMR (400 MHz, DMSO): δ1.45 (m, 1H), 1.95 (m, 1H), 2.15 (d, 2H), 2.20 (m, 3H), 2.35 (m, 1H), 2.70 (m, 1H), 5.05 (m, 1H), 7.30 (s, 2H), 8.15 (s, 1H), 8.35 (s, 1H), 8.85 (s, 1H), 10.50 (s, 1H).

(1S, 3S)-1-(9-Adenenyl)-3-carboxymethylcyclopentane (55).

Compound 55 was prepared by subjecting compound 53 to general procedure C. Yield=83%. TLC: $R_f$=0.33 (CHCl₃/MeOH/H₂O 150/45/5). Purity: >80% (HPLC method C). ¹H NMR (400 MHz, DMSO): δ1.45 (m, 1H), 1.95 (m, 1H), 2.15–2.40 (m, 4H), 2.45 (d, 2H), 2.70 (m, 1H), 5.05 (m, 1H), 7.30 (s, 2H), 8.25 (s, 1H), 8.35 (s, 1H).

(1R, 3S)-1-Chloro-3-(tert-Butyl-dimethylsiloxy)-4-cyclopentene (56).

Compound 56 was prepared by subjecting compound 22 to general procedure L. Yield=99%. TLC: $R_f$=0.86 (10% EtOAc/Hexane). ¹H NMR (400 MHz, CDCl₃): δ0.10 (s, 6H), 0.90 (s, 9H), 1.95 (m, 1H), 2.90 (m, 1H), 4.75 (m, 2H), 5.90 (m, 2H).

(1S, 3S)-1-(2-Dimethylmalonyl)-3-(tert-Butyl-dimethylsiloxy)-4-cyclopentene (57).

Compound 57 was prepared by subjecting compound 56 to general procedure M. Yield=75%. TLC: $R_f$=0.36 (10% EtOAc/Hexane). ¹H NMR (400 MHz, CDCl₃): δ0.05 (s, 6H), 0.90 (s, 9H), 1.95 (m, 2H), 3.20 (d, 1H), 3.55 (m, 1H), 3.75 (s, 6H), 4.90 (m, 1H), 5.80 (m, 2H).

(1S, 3R)-1-Hydroxy-3-(methyl-carboxymethyl)-4-cyclopentene (58).

Compound 57 was subjected to general procedure N. Yield=74%. TLC: $R_f$=0.58 (10% EtOAc/Hexane). ¹H NMR (400 MHz, DMSO): δ0.20 (s, 6H), 0.95 (s, 9H), 1.80 (m, 1H), 1.95 (m, 1H), 2.40 (m, 1H), 2.45 (m, 1H), 3.20 (m, 1H), 3.70 (s, 3H), 500 (m, 1H), 5.85 (m, 1H), 5.95 (m, 1H). Subsequent subjection of the product to general procedure K gave compound 58. Yield=59%. TLC: $R_f$=0.40 (50% EtOAc/Hexane). ¹H NMR (400 MHz, CDCl₃): δ1.85 (m, 1H), 2.00 (m, 1H), 2.35 (m, 2H), 3.30 (m, 1H), 3.65 (s, 3H), 4.90 (m, 1H), 5.85 (m, 1H), 5.95 (m, 1H).

(1R, 3R)-1-(9-Adenenyl)-3-(methyl-carboxymethyl)-4-cyclopentene (59).

Compound 59 was prepared by subjecting compound 58 to general procedure F. Yield=4.3%. TLC: $R_f$=0.17 (5% MeOH/CHCl₃). Purity: >81% (HPLC method C). ¹H NMR (400 MHz, DMSO): δ1.75 (m, 1H), 2.62 (m, 1H), 2.75 (m, 1H), 2.95 (m, 1H), 3.25 (m, 1H), 3.75 (s, 3H), 5.70 (m, 1H), 6.05 (m, 1H), 6.20 (m, 1H), 7.35 (s, 2H), 8.20 (s, 1H), 8.25 (s, 1H).

(1R, 3R)-1-(9-Adenenyl)-3-(N-hydroxycarbamoylmethyl)-4-cyclopentene (60) and (1R, 3R)-1-(9-Adenenyl)-3-carboxymethyl-4-cyclopentene (61).

Compound 59 was subjected to general procedure B and the products were separated by preparative TLC (CHCl₃/MeOH/H₂O 150/45/5). Hydroxamic acid (60): Yield=21%. TLC: $R_f$=0.29 (CHCl₃/MeOH/H₂O 150/45/5). Purity: >90% (HPLC method C). ¹H NMR (400 MHz, DMSO): δ1.75 (m, 1H), 2.20 (m, 1H), 2.35 (m, 1H), 2.90 (m, 1H), 3.25 (m, 1H), 5.70 (m, 1H), 6.05 (m, 1H), 6.20 (m, 1H), 7.35 (s, 2H), 8.15 (s, 1H), 8.25 (s, 1H), 9.10 (s, 1H), 10.60 (s, 1H). Carboxylic acid (61): Yield=31%. TLC: $R_f$=0.25 (CHCl₃/MeOH/H₂O 150/45/5). Purity: >99% (HPLC method C). ¹H NMR (400 MHz, DMSO): δ1.70 (m, 1H), 2.20 (m, 1H), 2.30 (m, 1H), 2.90 (m, 1H), 3.20 (m, 1H), 5.65 (m, 1H), 6.00 (m, 1H), 6.35 (m, 1H), 7.35 (s, 2H), 8.15 (s, 1H), 8.25 (s, 1H).

(1S, 3R)-1-(9-Adenenyl)-3-(methyl-carboxymethyl)cyclopentane (62).

Compound 62 was prepared by subjecting compound 59 to general procedure G. Yield=85%. TLC: $R_f$=0.27 (5% MeOH/CHCl₃). ¹H NMR (400 MHz, DMSO): δ1.72 (m, 1H), 1.88 (m, 1H), 2.04 (m, 1H), 2.16 (m, 1H), 2.28 (m, 1H), 2.46 (m, 2H), 3.70 (s, 3H), 4.95 (m, 1H), 7.30 (s, 2H), 8.25 (s, 1H), 8.35 (s, 1H).

(1S, 3R)-1-(9-Adenenyl)-3-(N-hydroxycarbamoylmethyl)cyclopentane (63) and (1S, 3R)-1-(9-Adenenyl)-3-carboxymethylcyclopentane (64).

Compound 62 was subjected to general procedure B and the products were separated by preparative HPLC and isolated as TFA salts. Hydroxamic acid (63): Yield=32%. TLC: $R_f$=0.33 (CHCl₃/MeOH/H₂O 150/45/5). Purity: >90% (HPLC method C). ¹H NMR (400 MHz, DMSO): δ1.70 (m, 1H), 1.85 (m, 1H), 2.00 (m, 1H), 2.20 (m, 1H), 2.25 (m, 2H), 2.30 (m, 1H), 2.45 (m, 2H), 5.00 (m, 1H), 8.45 (s, 1H), 8.55 (s, 1H). Carboxylic acid (64): Yield=11%. TLC: $R_f$=0.33 (CHCl₃/MeOH/H₂O 150/45/5). Purity: >95% (HPLC method C). ¹H NMR (400 MHz, DMSO): δ1.70 (m, 1H), 1.85 (m, 1H), 2.05 (m, 1H), 2.15 (m, 1H), 2.30 (m, 1H), 2.45 (m, 1H), 2.50 (m, 3H), 5.05 (m, 1H), 8.50 (s, 1H), 8.60 (s, 1H).

(1R, 3R)-1-Hydroxy-3-triphenylmethoxy-4-cyclopentene (65).

Compound 37 was subjected to general procedure J. TLC: $R_f$=0.36 (10% EtOAc/Hexane). 1H NMR (400 MHz, DMSO): δ2.00 (m, 1H), 2.15 (m, 1H), 4.95 (m, 1H), 5.40 (m, 1H), 5.95 (m, 1H), 6.05 (m, 1H), 7.30–7.60 (m, 15H), 8.20 (d, 2H), 8.40 (d, 2H). Subsequent subjection of the product to general procedure E gave compound 65. Yield=77% (2 steps). TLC: $R_f$=0.32 (25% EtOAc/Hexane). ¹H NMR (400 MHz, DMSO): δ1.55 (m, 1H), 1.80 (m, 1H), 4.70 (m, 1H), 4.80 (m, 1H), 5.10 (m, 1H), 5.80 (m, 1H), 7.40 (m, 3H), 7.45 (m, 6H), 7.55 (m, 6H).

(1S, 3R)-1-Chloro-3-triphenylmethoxy-4-cyclopentene (66).

Compound 66 was prepared by subjecting compound 65 to general procedure L. Yield=93%. TLC: $R_f$=0.58 (10% EtOAc/Hexane). $^1$H NMR (400 MHz, CDCl$_3$): δ1.90 (m, 1H), 2.40 (m, 1H), 4.55 (m, 2H), 5.20 (m, 1H), 5.75 (m, 1H), 7.20 (m, 3H), 7.25 (t, 6H), 7.50 (d, 6H).

(1R, 3R)-1-(2-Dimethylmalonyl)-3-triphenylmethoxy-4-cyclopentene (67).

Compound 67 was prepared by subjecting compound 66 to general procedure M. Yield=74%. TLC: $R_f$=0.22 (10% EtOAc/Hexane). $^1$H NMR (400 MHz, DMSO): δ1.60 (m, 1H), 1.80 (m, 1H), 3.70 (s, 3H), 3.71 (s, 3H), 4.70 (m, 1H), 5.00 (m, 1H), 5.75 (m, 1H), 7.40 (m, 3H), 7.45 (t, 6H), 7.55 (d, 6H).

(1R, 3S)-1-Hydroxy-3-(methyl-carboxymethyl)-4-cyclopentene (68).

Compound 67 was subjected to general procedure N. Yield=63%. TLC: $R_f$=0.45 (10% EtOAc/Hexane). $^1$H NMR (400 MHz, CDCl$_3$): δ1.45 (m, 1H), 1.90 (m, 1H), 2.15 (m, 2H), 3.15 (m, 1H), 3.60 (s, 3H), 4.70 (m, 1H), 4.80 (m, 1H), 5.70 (m, 1H), 7.20 (m, 3H), 7.25 (t, 6H), 7.45 (d, 6H). Subsequent subjection of the product to general procedure P gave compound 68. Yield=54%. TLC: $R_f$=0.35 (50% EtOAc/Hexane). $^1$H NMR (400 MHz, CDCl$_3$): δ1.40 (m, 1H), 1.85 (m, 1H), 2.00 (m, 1H), 2.35 (m, 2H), 3.30 (m, 1H), 3.65 (s, 3H), 4.85 (m, 1H), 5.85 (m, 1H), 5.95 (m, 1H).

(1S, 3S)-1-(9-Adenenyl)-3-(methyl-carboxymethyl)-4-cyclopentene (69).

Compound 69 was prepared by subjecting compound 68 to general procedure F. Yield=16%. TLC: $R_f$=0.17 (5% MeOH/CHCl$_3$). Purity: >87% (HPLC method C). $^1$H NMR (400 MHz, DMSO): δ1.75 (m, 1H), 2.62 (m, 1H), 2.75 (m, 1H), 2.95 (m, 1H), 3.25 (m, 1H), 3.75 (s, 3H), 5.70 (m, 1H), 6.05 (m, 1H), 6.20 (m, 1H), 7.35 (s, 2H) 8.20 (s, 1H), 8.25 (s, 1H).

(1S, 3S)-1-(9-Adenenyl)-3-(N-hydroxycarbamoylmethyl)-4-cyclopentene (70).

Compound 70 was prepared by subjecting compound 69 to general procedure B. Yield=49%. TLC: $R_f$=0.36 (CHCl$_3$/MeOH/H$_2$O 150/45/5). Purity: >89% (HPLC method C). $^1$H NMR (400 MHz, DMSO): δ1.75 (m, 1H), 2.20 (m, 1H), 2.35 (m, 1H), 2.90 (m, 1H), 3.25 (m, 1H), 5.70 (m, 1H), 6.05 (m, 1H), 6.20 (m, 1H), 7.35 (s, 2H), 8.15 (s, 1H), 8.25 (s, 1H), 8.90 (s, 1H), 10.50 (s, 1H).

(1S, 3S)-1-(9-Adenenyl)-3-carboxymethyl-4-cyclopentene (71).

Compound 71 was prepared by subjecting compound 69 to general procedure C. Yield=75%. TLC: $R_f$=0.34 (CHCl$_3$/MeOH/H$_2$O 150/45/5). Purity: >84% (HPLC method C). $^1$H NMR (400 MHz, DMSO): δ1.70 (m, 1H), 2.30 (m, 1H), 2.45 (m, 1H), 2.90 (m, 1H), 3.20 (m, 1H), 5.65 (m, 1H), 6.00 (m, 1H), 6.25 (m, 1H), 7.35 (s, 2H), 8.15 (s, 1H), 8.25 (s, 1H).

(1R, 3S)-1-(9-Adenenyl)-3-(methyl-carboxymethyl)cyclopentane (72).

Compound 72 was prepared by subjecting compound 69 to general procedure G. Yield=92%. TLC: $R_f$=0.27 (5% MeOH/CHCl$_3$). Purity: >87% (HPLC method C). $^1$H NMR (400 MHz, DMSO): δ1.72 (m, 1H), 1.88 (m, 1H), 2.04 (m, 1), 2.16 (m, 1H), 2.28 (m, 1H), 2.46 (m, 2H), 2.62 (m, 2H), 3.70 (s, 3H), 4.95 (m, 1H), 7.30 (s, 2H) 8.25 (s, 1H), 8.35 (s, 1H).

(1R, 3S)-1-(9-Adenenyl)-3-(N-hydroxycarbamoylmethyl)cyclopentane (73).

Compound 73 was prepared by subjecting compound 72 to general procedure B. Yield=56%. TLC: $R_f$=0.42 (CHCl$_3$/MeOH/H2O 150/45/5). Purity: >94% (HPLC method C). $^1$H NMR (400 MHz, DMSO): δ1.70 (m, 1H), 1.85 (m, 1H), 2.00 (m, 1H), 2.20 (m, 1H), 2.25 (m, 2H), 2.30 (m, 1H), 2.45 (m, 2H), 4.95 (m, 1H), 7.30 (s, 2H), 8.25 (s, 1H), 8.35 (s, 1H), 8.85 (bs, 1H), 10.50 (bs, 1H).

(1R, 3S)-1-(9-Adenenyl)-3-carboxymethylcyclopentane (74).

Compound 74 was prepared by subjecting compound 72 to general procedure C. Yield=99%. TLC: $R_f$=0.42 (CHCl$_3$/MeOH/H$_2$O 150/45/5). Purity: >82% (HPLC method C). $^1$H NMR (400 MHz, DMSO): δ1.70 (m, 1H), 1.85 (m, 1H), 2.05 (m, 1H), 2.15 (m, 1H), 2.30 (m, 1H), 2.45 (m, 4H), 4.95 (m, 1H), 7.35 (s, 2H), 8.20 (s, 1H), 8.35 (s, 1H).

(1S, 3R)-Methyl-1-aminocyclopent-4-ene-3-carboxylate hydrochloride (76a).

Compound 76a was prepared by subjecting (1S, 3R)-1-aminocyclopent-4-ene-3-carboxylic acid to general procedure Q. Yield=100%. $^1$H NMR (400 MHz, DMSO): δ2.05 (m, 1H), 2.65 (m, 1H), 3.80 (s, 3H), 3.85 (m, 1H), 4.30 (m, 1H), 6.00 (m, 1H), 6.20 (m, 1H), 8.40 (bs, 3H).

(1R, 3S)-Methyl-1-aminocyclopent-4-ene-3-carboxylate hydrochloride (76b).

Compound 76b was prepared by subjecting (1R, 3S)-1-aminocyclopent-4-ene-3-carboxylic acid to general procedure Q. Yield=100%. $^1$H NMR (400 MHz, DMSO): δ2.05 (m 1H), 2.65 (m, 1H), 3.80 (s, 3H), 3.85 (m, 1H), 4.30 (m, 1H), 6.00 (m, 1H), 6.20 (m, 1H), 8.40 (bs, 3H).

(1S, 3R)-1-[9-(1-Chloroadenenyl)]-3-methylcarboxy-4cyclopentene (77a).

Compound 76a was subjected to general procedure R. Subsequent subjection of the crude product to general procedure S yielded the desired crude aminopyrimidine. Without purification, the crude aminopyrimidine was subjected to general procedure T giving compound 77a. Yield=40% (3 steps). TLC: $R_f$=0.50 (EtOAc/Hexane). Purity: >90% (HPLC method C). $^1$H NMR (400 MHz, DMSO): δ2.35 (m, 1H), 3.00 (m, 1H), 3.80 (s, 3H), 3.95 (m, 1H), 5.90 (m, 1H), 6.25 (m, 1H), 6.40 (m, 1H), 8.65 (s, 1H), 8.90 (s, 1H).

(1R, 3S)-1-[9-(1-Chloroadenenyl)]-3-methylcarboxy-4-cyclopentene (77b).

Compound 76b was subjected to general procedure R. Subsequent subjection of the crude product to general procedure S yielded the desired crude arinopyrimidine. Without purification, the crude aminopyrimidine was subjected to general procedure T giving compound 77b. Yield=38% (3 steps). TLC: $R_f$=0.50 (EtOAc/Hexane). Purity: >90% (HPLC method C). $^2$H NMR (400 MHz, DMSO): δ2.35 (m, 1H), 3.00 (m, 1H), 3.80 (s, 3H), 3.95 (m, 1H), 5.90 (m, 1H), 6.25 (m, 1H), 6.40 (m, 1H), 8.65 (s, 1H), 8.90 (s, 1H).

(1S, 3R)-1-[9-(1-Azidoadenenyl)]-3-methylcarboxy-4-cyclopentene (78a).

Compound 78a was prepared by subjecting compound 77a to general procedure U. Yield=52%. Purity: >99% (HPLC method C). $^1$H NMR (400 MHz, DMSO): δ2.40 (m, 1H), 3.05 (m, 1H), 3.80 (s, 3H), 4.00 (m, 1H), 6.00 (m, 1H), 6.30 (m, 1H), 6.45 (m, 1H), 8.60 (m, 1H), 10.25 (s, 1H).

(1R, 3S)-1-[9-(1-Azidoadenenyl)]-3-methylcarboxy-4-cyclopentene (78b).

Compound 78b was prepared by subjecting compound 77b to general procedure U. Yield=60%. Purity: >99% (HPLC method C). $^1$H NMR (400 MHz, DMSO): δ2.40 (m, 1H), 3.05 (m, 1H), 3.80 (s, 3H), 4.00 (m, 1H), 6.00 (m, 1H), 6.30 (m, 1H), 6.45 (m, 1H), 8.60 (m, 1H), 10.25 (s, 1H).

(1R, 3S)-1-(9-Adenenyl)-3-methylcarboxycyclopentane (79a).

Compound 79a was prepared by subjecting compound 78a to general procedure G. Yield=99%. Purity: >99% (HPLC method C). $^1$H NMR (400 MHz, DMSO): δ2.20 (m, 3H), 2.30 (m, 1H), 2.40 (m, 1H), 2.55 (m, 1H), 3.15 (m, 1H), 3.80 (s, 3H), 5.00 (m, 1H), 7.35 (s, 2H), 8.20 (m, 1H), 8.35 (s, 1H).

(1S, 3R)-1-(9-Adenenyl)-3-methylcarboxycyclopentane (79b).

Compound 79b was prepared by subjecting compound 78b to general procedure G. Yield=96%. Purity: >99% (HPLC method C). $^1$H NMR (400 MHz, DMSO): δ2.20 (m, 3H), 2.30 (m, 1H), 2.40 (m, 1H), 2.55 (m, 1H), 3.15 (m, 1H), 3.80 (s, 3H), 5.00 (m, 1H), 7.35 (s, 2H), 8.20 (m, 1H), 8.35 (s, 1H).

(1R, 3S)-1-(9-Adenenyl)-3-(N-hydroxycarbamoyl)cyclopentane (80a).

Compound 80a was prepared by subjecting compound 79a to general procedure B. Yield=53%. Purity: >95% (HPLC method C). $^1$H NMR (400 MHz, DMSO): δ2.00 (m, 2H), 2.30 (m, 3H), 2.50 (m, 1H), 2.80 (m, 1H), 5.00 (m, 1H), 7.35 (s, 2H), 8.25 (m, 1H), 8.45 (s, 1H), 8.95 (s, 1H), 10.65 (s, 1H).

(1S, 3R)-1-(9-Adenenyl)-3-(N-hydroxycarbamoyl)cyclopentane (80b).

Compound 80b was prepared by subjecting compound 79b to general procedure B. Yield=53%. Purity: >95% (HPLC method C). $^1$H NMR (400 MHz, DMSO): δ2.00 (m, 2H), 2.30 (m, 3H), 2.50 (m, 1H), 2.80 (m, 1H), 5.00 (m, 1H), 7.35 (s, 2H), 8.25 (s, 1H), 8.45 (s, 1H), 8.95 (s, 1H), 10.65 (s, 1H).

(1R, 3S)-1-(9-Adenenyl)-3-carboxycyclopentane (81a).

Compound 81a was prepared by subjecting compound 79a to general procedure C. Yield=60%. Purity: >99% (HPLC method C). 1H NMR (400 MHz, DMSO): δ2.10–2.40 (m, 5H), 2.55 (m, 1H), 3.05 (m, 1H), 5.00 (m, 1H), 7.35 (s, 2H), 8.25 (s, 1H), 8.35 (s, 1H), 12.40 (s, 1H).

(1S, 3R)-1-(9-Adenenyl)-3-carboxycyclopentane (81b).

Compound 81b was prepared by subjecting compound 79b to general procedure C. Yield=58%. Purity: >99% (HPLC method C). $^1$H NMR (400 MHz, DMSO): δ2.10–2.40 (m, 5H), 2.55 (m, 1H), 3.05 (m, 1H), 5.00 (m, 1H), 7.35 (s, 2H), 8.25 (s, 1H), 8.35 (s, 1H), 12.40 (s, 1H).

(1S, 3R)-1-(9-Adenenyl)-3-methylcarboxy-4-cyclopentene (82a).

Compound 82a was prepared by subjecting compound 78a to general procedure V. Yield=98%. Purity: >99% (HPLC method C). $^1$H NMR (400 MHz, DMSO): δ2.25 (m, 1H), 2.95 (m, 1H), 3.75 (s, 3H), 3.90 (m, 1H), 5.75 (m, 1H), 6.20 (m, 1H), 6.30 (m, 1), 7.35 (s, 2H), 8.05 (s, 1H), 8.25 (s, 1H).

(1R, 3S)-1-(9-Adenenyl)-3-methylcarboxy-4-cyclopentene (82b).

Compound 82b was prepared by subjecting compound 78b to general procedure V. Yield=97%. Purity: >99% (HPLC method C). $^1$H NMR (400 MHz, DMSO): δ2.25 (m, 1H), 2.95 (m, 1H), 3.75 (s, 3H), 3.90 (m, 1H), 5.75 (m, 1H), 6.20 (m, 1H), 6.30 (m, 1H), 7.35 (s, 2H), 8.05 (s, 1H), 8.25 (s, 1H).

(1S, 3R)-1-(9-Adenenyl)-3-(N-hydroxycarbamoyl)-4-cyclopentene (83a) and (1S, 3S)-1-(9-Adenenyl)-3-(N-hydroxycarbamoyl)-4-cyclopentene (84a).

Compound 82a was subjected to general procedure B and the products were separated by preparative HPLC as described. The isolated TFA salts were converted to free bases utilizing MP-carbonate resin (Argonaut) in MeOH. Compound 83a: Yield=44%. TLC: $R_f$=0.34 (CHCl$_3$/MeOH/H$_2$O 150/45/5). Purity: >99% (HPLC method C). $^1$H NMR (400 MHz, DMSO): δ2.10 (m, 1H), 2.90 (m, 1H), 3.55 (m, 1H), 5.80 (m, 1H), 6.15 (m, 1H), 6.20 (m, 1H), 7.35 (s, 2H), 8.25 (s, 1H), 8.35 (s, 1H), 9.05 (bs, 1H), 10.80 (bs, 1H).

Compound 84a: Yield=26%. TLC: $R_f$=0.29 (CHCl$_3$/MeOH/H$_2$O 150/45/5). Purity: >99% (HPLC method C). $^1$H NMR (400 MHz, DMSO): δ2.30 (m, 1H), 2.75 (m, 1H), 3.85 (m, 1H), 5.85 (m, 1H), 6.15 (m, 1H), 6.20 (m, 1H), 7.35 (s, 2H), 8.15 (s, 1H), 8.25 (s, 1H), 9.00 (s, 1H), 10.80 (s, 1H).

(1R, 3S)-1-(9-Adenenyl)-3-(N-hydroxycarbamoyl)-4-cyclopentene (83b) and (1R, 3R)-1-(9-Adenenyl)-3-(N-hydroxycarbamoyl)-4-cyclopentene (84b).

Compound 82b was subjected to general procedure B and the products were separated by preparative HPLC as described. The isolated TFA salts were converted to free bases utilizing MP-carbonate resin (Argonaut) in MeOH. Compound 83b: Yield=44%. TLC: $R_f$=0.32 (CHCl$_3$/MeOH/H$_2$O 150/45/5). Purity: >99% (HPLC method C). $^1$H NMR (400 MHz, DMSO): δ2.10 (m, 1H), 2.90 (m, 1H), 3.55 (m, 1H), 5.80 (m, 1H), 6.15 (m, 1H), 6.20 (m, 1H), 7.35 (s, 2H), 8.25 (s, 1H), 8.35 (s, 1H), 9.05 (bs, 1H), 10.80 (bs, 1H).

Compound 84b: Yield=24%. TLC: $R_f$=0.26 (CHCl$_3$/MeOH/H$_2$O 150/45/5). Purity: >99% (HPLC method C). $^1$H NMR (400 MHz, DMSO): δ2.30 (m, 1H), 2.75 (m, 1H), 3.85 (m, 1H), 5.85 (m, 1H), 6.15 (m, 1H), 6.20 (m, 1H), 7.35 (s, 2H), 8.15 (s, 1), 8.25 (s, 1H), 9.00 (bs, 1H), 10.80 (bs, 1H).

(1R, 3R)-1-(9-Adenenyl)-3-(N-hydroxycarbamoyl)cyclopentane (85a).

Compound 85a was prepared by subjecting compound 84a to general procedure G where 10% Pd/C was replaced with 20% Pd(OH)$_2$/C. Yield=99%. TLC: $R_f$=0.27 (CHCl$_3$/MeOH/H$_2$O 150/45/5). Purity: >97% (BPLC method C). $^1$H NMR (400 MHz, DMSO): δ1.90 (m, 1H), 2.15–2.40 (m, 5H), 2.95 (m, 1H), 5.05 (m, 1H), 7.30 (s, 2H), 8.25 (s, 1H), 8.30 (s, 1H), 8.90 (s, 1H), 10.60 (s, 1H).

(1S, 3S)-1-(9-Adenenyl)-3-(N-hydroxycarbamoyl)cyclopentane (85b).

Compound 85b was prepared by subjecting compound 84b to general procedure G where 10% Pd/C was replaced with 20% Pd(OH)$_2$/C. Yield=95%. TLC: $R_f$=0.27 (CHCl$_3$/MeOH/H$_2$O 150/45/5). Purity: >97% (HPLC method C). $^1$H NMR (400 MHz, DMSO): δ1.90 (m, 1H), 2.15–2.40 (m, 5H), 2.95 (m, 1H), 5.05 (m, 1H), 7.30 (s, 2H), 8.25 (s, 1H), 8.30 (s, 1H), 8.90 (s, 1H), 10.60 (s, 1H).

(1S, 3R)-1-(9-Adenenyl)-3-carboxy-4-cyclopentene (86a) and (1S, 3S)-1-(9-Adenenyl)-3-carboxy-4-cyclopentene (87a) and (1R, 3)-1-(9-Adenenyl)-3-carboxy-3-cyclopentene (88a).

Compound 82a was subjected to general procedure C yielding a mixture of compounds 86a, 87a and 88a. Utilizing preparative HPLC (0–10% CH$_3$CN/30 minutes), compound 86a was separated from compounds 87a and 88a. Compounds 87a and 88a could not be separated from one another. All compounds were isolated as TFA salts. Compound 86a: Yield=30%. TLC: $R_f$=0.19 (CHCl$_3$/MeOH/H$_2$O 150/45/5). Purity: >84% (HPLC method C). $^1$H NMR (400 MHz, DMSO): δ2.25 (m, 1H), 2.95 (m, 1H), 3.85 (m, 1H), 5.80 (m, 1H), 6.20 (m, 1H), 6.40 (m, 1H), 8.30 (s, 1H), 8.50 (m, 3H). Compounds 87a and 88a: Yield=60%. 87a/88a=4/5. TLC: $R_f$=0.19 (CHCl$_3$/MeOH/H$_2$O 150/45/5). Purity: >99% (HPLC method C). $^1$H NMR (400 MHz, DMSO): δ2.35 (m, 1H, 87a), 2.85 (m, 1H, 87a), 3.05 (m, 2H, 88a), 3.25 (m, 2H, 88a), 4.15 (m, 1H, 87a), 5.45 (m, 1H, 88a), 5.90 (m, 1H, 87a), 6.15 (m, 1H, 87a), 6.35 (m, 1H, 87a), 6.90 (m, 1H, 88a), 8.40 (s, 1H, 87a), 8.50 (s, 1H, 87a), 8.50 (s, 1H, 88a), 8.55 (s, 1H, 88a), 8.60 (bs, 2H, 87a), 8.60 (bs, 2H, 88a).

(1R, 3S)-1-(9-Adenenyl)-3-carboxy-4-cyclopentene (86b) and (1R, 3R)-1-(9-Adenenyl)-3-carboxy-4-cyclopentene (87b) and (1S)-1-(9-Adenenyl)-3-carboxy-3-cyclopentene (88b).

Compound 82b was subjected to general procedure C yielding a mixture of compounds 86b, 87b and 88b. Utilizing preparative HPLC (0–10% $CH_3CN$/30 minutes), compound 86b was separated from compounds 87b and 88b. Compounds 87b and 88b could not be separated from one another. All compounds were isolated as TFA salts. Compound 86b: Yield=41%. TLC: $R_f$=0.20 ($CHCl_3$/MeOH/$H_2O$ 150/45/5). Purity: >93% (HPLC method C). $^1$H NMR (400 MHz, DMSO): δ2.25 (m, 1H), 2.95 (m, 1H), 3.85 (m, 1H), 5.80 (m, 1H), 6.20 (m, 1H), 6.40 (m, 1H), 8.30 (s, 1H), 8.50 (s, 1H), 8.85 (bs, 2H). Compounds 87b and 88b: Yield=68%. 87b/88b=1/2. TLC: $R_f$=0.20 ($CHCl_3$/MeOH/$H_2O$ 150/45/5). Purity: >99% (HPLC method C). $^1$H NMR (400 MHz, DMSO): δ2.35 (m, 1H, 87b), 2.85 (m, 1H, 87b), 3.05 (m, 2H, 88b), 3.25 (m, 2H, 88b), 4.15 (m, 1H, 87b), 5.45 (m, 1H, 88b), 5.90 (m, 1H, 87b), 6.15 (m, 1H, 87b), 6.35 (m, 1H, 87b), 6.90 (m, 1H, 88b), 8.40 (s, 1H, 87b), 8.50 (s, 1H, 87b), 8.50 (s, 1H, 88b), 8.55 (s, 1H, 88b), 8.60 (bs, 2H, 87b), 8.60 (bs, 2H, 88b).

Biological Assays

For measurement of adenylyl cyclase activities, is is ideal to utilize a cell line which over-expresses human type V recombinant Adenylyl Cyclase (AC) as compared to ordinary cells. Preferably the AC is expressed in the cell line HEK293. Membranes isolated from these cells which have been transfected with a DNA fragment encoding AC can demonstrate a 40–50 fold stimulation by recombinant activated Gs-alpha when compared to empty vector (pcDNA3), control populations of this cell line. Stimulation with activated Gs-alpha can be used to demonstrate that 90–98% of the cAMP generation in the human AC V populations is due to expression of the recombinant adenylyl cyclase.

Type V AC activity for compounds according to the invention is evaluated in an AC transfected cell line (transfected as described above, for example) with added control inhibitors (positive control) or without added control inhibitors (negative control) or with an added compound according to the invention. The assay can be adapted to follow an established protocol for AC expression, an example, of which, is summarized generally herein for clarity. Membranes (140 ng/ml) are used in the presence of a control incubation solution 60 mM HEPES, pH 8.0, 0.6 mM EDTA, 0.01% (w/v) Bovine serum albumin, 25 nM activated recombinant Gs-alpha, 1 mM ATP, 2 mM isobutyl methyl xanthine and 2 mM $MgCl_2$. To this control solution may be added a positive control compound or a compound according to the present invention and the mixture is incubated for 30 minutes at 30 degrees Centigrade. Upon termination of incubation, the mixture is evaluated for the enzymatic product, cAMP using a commercially available New England Nuclear flash plate system. The degree of inhibition for the positive control or a compound according to the present invention is determined by comparing the results from the positive control or compound according to the invention to results from the negative control which utilized only the incubation solution without any positive control or compound according to the present invention.

The compounds of formula (I) and pharmaceutically acceptable salts thereof can be administered as such, but it is usually preferred to administer them in the form of pharmaceutical compositions, which are used for animals and human beings.

Compositions or formulations of the compounds of the invention are prepared for storage or administration by mixing the compound having a desired degree of purity with physiologically acceptable carriers, excipients, stabilizers etc., and may be provided in sustained release or timed release formulations. Acceptable carriers or diluents for therapeutic use are well known in the pharmaceutical field, and are described, for example, in Remington's Pharmaceutical Sciences, Mack Publishing Co., (A. R. Gennaro edit. 1985). Such materials are nontoxic to the recipients at the dosages and concentrations employed, and include buffers such as phosphate, citrate, acetate and other organic acid salts, antioxidants such as ascorbic acid, low molecular weight (less than about ten residues) peptides such as polyarginine, proteins, such as serum albumin, gelatin, or immunoglobulins, hydrophilic polymers such as polyvinylpyrrolidinone, amino acids such as glycine, glutamic acid, aspartic acid, or arginine, monosaccharides, disaccharides, and other carbohydrates including cellulose or its derivatives, glucose, mannose or dextrins, chelating agents such as EDTA, sugar alcohols such as mannitol or sorbitol, counterions such as sodium and/or nonionic surfactants such as TWEEN®, PLURONICS® or polyethyleneglycol.

The term "effective amount" is an amount necessary for administering the compound in accordance with the present invention to provide the necessary effect such as inhibiting the phosphorylation of kinases or treating disease states in a mammal. In accordance with the present invention, a suitable single dose size is a dose that is capable of preventing or treating an animal with a disease when administered one or more times over a suitable time period. Doses can vary depending upon the disease being treated. For example, in the treatment of hypersensitivity, a suitable single dose can be dependent upon the nature of the immunogen causing the hypersensitivity.

An effective administration protocol (i.e., administering a therapeutic composition in an effective manner) comprises suitable dose parameters and modes of administration that result in prevention or treatment of a disease. Effective dose parameters and modes of administration can be determined using methods standard in the art for a particular disease. Such methods include, for example, determination of survival rates, side effects (i.e., toxicity) and progression or regression of disease. For example, the effectiveness of dose parameters and modes of administration of a therapeutic composition of the present invention can be determined by assessing response rates. Such response rates refer to the percentage of treated patients in a population of patients that respond with either partial or complete remission.

It is preferred to employ the administration route which is the most effective for the treatment. For example, administration is made orally or non-orally by intrarectal, intraoral, subcutaneous, intramuscular or intravenous administration.

Examples of the forms for administration are capsules, tablets, granules, powders, syrups, emulsions, suppositories and injections.

Liquid compositions such as emulsions and syrups which are appropriate for oral administration can be preparedusingwater, sugars such as sucrose, sorbitol and fructose, glycols such as polyethylene glycol and propylene glycol, oils such as sesame oil, olive oil and soybean oil, preservatives such as benzoates, flavors such as strawberry flavor and peppermint, etc.

Capsules, tablets, powders and granules can be prepared using excipients such as lactose, glucose, sucrose and mannitol, disintegrating agents such as starch and sodium alginate, lubricants such as magnesium stearate and talc, binders such as polyvinyl alcohol, hydroxypropyl cellulose and gelatin, surfactants such as fatty acid esters, plasticizers such as glycerin, etc.

Compositions suitable for non-oral administration preferably comprise a sterilized aqueous preparation containing an active compound which is isotonic to the recipient's blood. For example, injections are prepared using a carrier which comprises a salt solution, a glucose solution, or a mixture of a salt solution and a glucose solution.

Compositions for topical application are prepared by dissolving or suspending an active compound in one or more kinds of solvents such as mineral oil, petroleum and polyhydric alcohol, or other bases used for topical drugs.

Compositions for intestinal administration are prepared using ordinary carriers such as cacao fat, hydrogenated fat and hydrogenated fat carboxylic acid, and are provided as suppositories.

The compositions for non-oral administration may additionally be formulated to contain one or more kinds of additives selected from glycols, oils, flavors, preservatives (including antioxidants), excipients, disintegrating agents, lubricants, binders, surfactants and plasticizers which are used for the preparation of compositions for oral administration.

The effective dose and the administration schedule for each of the compounds of formula (I) or a pharmaceutically acceptable salt thereof will vary depending on the administration route, the patient's age and body weight, and the type or degree of the diseases to be treated. However, it is generally appropriate to administer a compound of formula (I) or a pharmaceutically acceptable salt thereof in a dose of 0.01–1000 mg/adult/day, preferably 5–500 mg/adult/day, in one to several parts.

All the compounds of the present invention can be immediately applied to the treatment of kinase-dependent diseases of mammals as kinase inhibitors, specifically, those relating to tyrosine kinase. Specifically preferred are the compounds which have IC50 within the range of 10 nM-10 $\mu$M. Even more preferred are compounds which have IC50 within the range of 10 $\mu$M to −1 $\mu$M. Most preferred are compounds which have an IC50 value which is smaller than 1 $\mu$M.

Specific compounds of the present invention which have an activity to specifically inhibit one of the three types of protein kinase (for example, kinase which phosphorylates tyrosine, kinase which phosphorylates tyrosine and threonine, and kinase which phosphorylates threonine) can be selected. Tyrosine kinase-dependent diseases include hyperproliferative malfunction which is caused or maintained by abnormal tyrosine kinase activity. Examples thereof include psoriasis, pulmonary fibrosis, glomerulonephritis, cancer, atherosclerosis and antiangiopoiesis (for example, tumor growth and diabetic retinopathy). Current knowledge of the relationship between other classes of kinase and specific diseases is insufficient. However, compounds having specific PTK-inhibiting activity have a useful treatment effect. Other classes of kinase have also been recognized in the same manner. Quercetin, genistein and staurosporin, which are all PTK-inhibitors, inhibit many kinds of protein kinase in addition to tyrosine kinase. However, as a result of their lack of the specificity, their cytotoxicity is high. Therefore, a PTK-inhibitor (or an inhibitor of other classes of kinase) which is apt to bring about undesirable side effects because of the lack of selectivity can be identified by the use of an ordinary test to measure cytotoxicity.

The present invention provides nitrogen-containing heterocyclic compounds and pharmaceutically acceptable salts thereof which inhibit phosphorylation of PDGF receptor to hinder abnormal cell growth and cell wandering and thus are useful for the prevention or treaLment of cell-proliferative diseases such as arteriosclerosis, vascular reobstruction, cancer and glomerulosclerosis.

Dosage formulations of the compounds of the invention to be used for therapeutic administration must be sterile. Sterility is readily accomplished by filtration through sterile membranes such as 0.2 micron membranes, or by other conventional methods. Formulations typically will be stored in lyophilized form or as an aqueous solution. The pH of the preparations of the invention typically will be about 3–11, more preferably about 5–9 and most preferably about 7–8. It will be understood that use of certain of the foregoing excipients, carriers, or stabilizers will result in the formation of cyclic polypeptide salts. While the preferred route of administration is by injection, other methods of administration are also anticipated such as orally, intravenously (bolus and/or infusion), subcutaneously, intramuscularly, colonically, rectally, nasally, transdermally or intraperitoneally, employing a variety of dosage forms such as suppositories, implanted pellets or small cylinders, aerosols, oral dosage formulations and topical formulations such as ointments, drops and dermal patches. The compounds of the invention are desirably incorporated into shaped articles such as implants which may employ inert materials such as biodegradable polymers or synthetic silicones, for example, Silastic, silicone rubber or other polymers commercially available.

The compounds of the invention may also be administered in the form of liposome delivery systems, such as small unilamellar vesicles, large unilamellar vesicles and multilamellar vesicles. Liposomes can be formed from a variety of lipids, such as cholesterol, stearylamine or phosphatidylcholines.

The compounds of the invention may also be delivered by the use of antibodies, antibody fragments, growth factors, hormones, or other targeting moieties, to which the compound molecules are coupled. The compounds of the invention may also be coupled with suitable polymers as targetable drug carriers. Such polymers can include polyvinylpyrrolidinone, pyran copolymer, polyhydroxypropyl-methacrylamide-phenol, polyhydroxyethyl-aspartamide-phenol, or polyethyleneoxide-polylysine substituted with palmitoyl residues. Furthermore, compounds of the invention may be coupled to a class of biodegradable polymers useful in achieving controlled release of a drug, for example polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels. Polymers and semipermeable polymer matrices may be formed into shaped articles, such as valves, stents, tubing, prostheses and the like.

Therapeutic compound liquid formulations generally are placed into a container having a sterile access port, for example, an intravenous solution bag or vial having a stopper pierceable by hypodermic injection needle.

Therapeutically effective dosages may be determined by either in vitro or in vivo methods. For each particular compound of the present invention, individual determina tions may be made to determine the optimal dosage required. The range of therapeutically effective dosages will be influenced by the route of administration, the therapeutic objectives and the condition of the patient. For injection by hypodermic needle, it may be assumed the dosage is delivered into the body's fluids. For other routes of administration, the absorption efficiency must be individually determined for each compound by methods well known in pharmacology. Accordingly, it may be necessary for the therapist to titer the dosage and modify the route of administration as required to obtain the optimal therapeutic effect. The determination of effective dosage levels, that is, the dosage levels necessary to achieve the desired result, will be readily determined by one skilled in the art. Typically, applications of compound are commenced at lower dosage levels, with dosage levels being increased until the desired effect is achieved.

The compounds and compositions of the invention can be administered orally or parenterally in an effective amount within the dosage range of about 0.001 to about 1000 mg/kg, preferably about 0.01 to about 100 mg/kg and more preferably about 0.1 to about 20 mg/kg. Advantageously, the compounds and composition of the invention may be administered several times daily. Other dosage regimens may also be useful (e.g. single daily dose and/or continuous infusion).

Typically, about 0.5 to about 500 mg of a compound or mixture of compounds of the invention, as the free acid or base form or as a pharmaceutically acceptable salt, is compounded with a physiologically acceptable vehicle, carrier, excipient, binder, preservative, stabilizer, dye, flavor etc., as called for by accepted pharmaceutical practice. The amount of active ingredient in these compositions is such that a suitable dosage in the range indicated is obtained.

Typical adjuvants which may be incorporated into tablets, capsules and the like are binders such as acacia, corn starch or gelatin, and excipients such as microcrystalline cellulose, disintegrating agents like corn starch or alginic acid, lubricants such as magnesium stearate, sweetening agents such as sucrose or lactose, or flavoring agents. When a dosage form is a capsule, in addition to the above materials it may also contain liquid carriers such as water, saline, or a fatty oil. Other materials of various types may be used as coatings or as modifiers of the physical form of the dosage unit. Sterile compositions for injection can be formulated according to conventional pharmaceutical practice. For example, dissolution or suspension of the active compound in a vehicle such as an oil or a synthetic fatty vehicle like ethyl oleate, or into a liposome may be desired. Buffers, preservatives, antioxidants and the like can be incorporated according to accepted pharmaceutical practice.

Without further description, it is believed that one of ordinary skill in the art can, using the preceding description and the illustrative examples, make and utilize the compounds of the present invention and practice the claimed methods. It should be understood that the foregoing discussion and examples merely present a detailed description of certain preferred embodiments. It will be apparent to those of ordinary skill in the art that various modifications and equivalents can be made without departing from the spirit and scope of the invention. All the patents, journal articles and other documents discussed or cited above are herein incorporated by reference.

What is claimed is:

1. A compound of the formula (I):

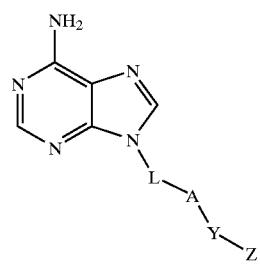

wherein:

A is a member selected from the group consisting of:
benzene, thiophene, furan, pyrrole, indole,

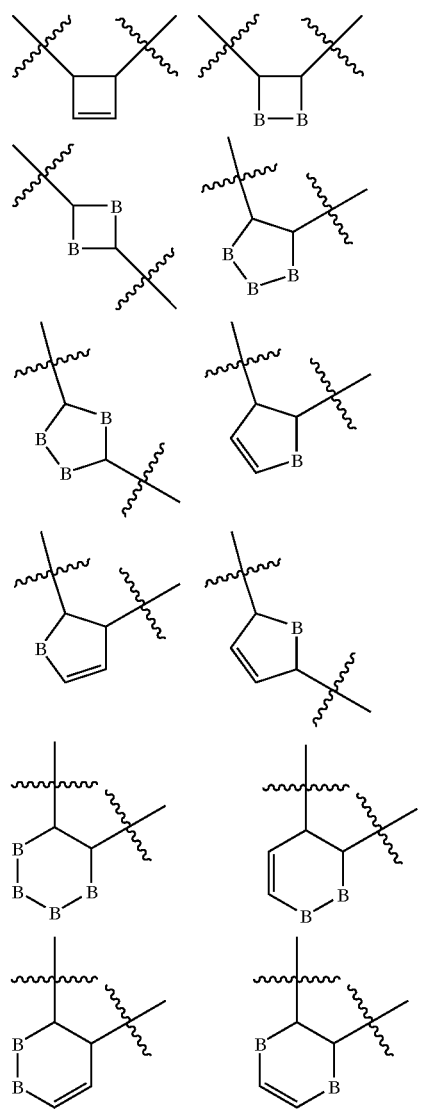

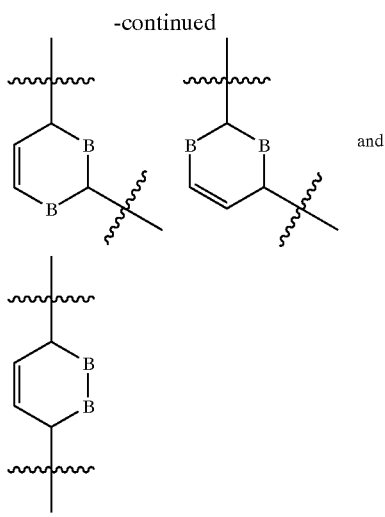

wherein
- each B is independently selected from the group consisting of —C(—R$^1$)(—R$^2$)—, —O— and —N(—J—R$^3$)—, wherein not more than one B in any ring is either —O— or —N(—J—R$^3$)—;
- each m is independently an integer from 0 to 4;
- each n is independently an integer from 1 to 4;
- each q is independently an integer from 0 to 8;
- Y is a member selected from the group consisting of —(CH$_2$)$_q$—, —(CH$_2$)$_m$O— and —(CH$_2$)$_m$—N(—J$^1$—)—R$^4$;
- Z is a member selected from the group consisting of —(CH$_2$)$_n$—C(=O)—NHOH, —(CH$_2$)$_n$COOH, —(CH$_2$)$_n$COOMe and —(CH$_2$)$_n$COOEt;
- L is a member selected from the group consisting of —(CH$_2$)$_q$—, —(CH$_2$)$_m$O— and —(CH$_2$)$_m$—N—(—J$^2$—)—R$^5$;
- J, J$^1$ and J$^2$ are each independently selected from the group consisting of C(=O) and a bond;
- R$^1$ is a member selected from the group consisting of H, —N(—J$^3$—R$^6$)(—J$^4$—R$^7$) and —O—J$^5$—R$^8$, wherein J$^3$, J$^4$ and J$^5$ are each independently selected from the group consisting of —C(=O)— and a bond, wherein at least one of J$^3$ and J$^4$ is a bond;
- R$^2$ is a member selected from the group consisting of H, —N(—J$^6$—R$^9$)(—J$^7$—R$^{10}$) and —O—J$^8$—R$^{11}$, wherein J$^6$, J$^7$ and J$^8$ are independently selected from the group consisting of —C(=O)— and a bond, wherein at least one of J$^6$ and J$^7$ is a bond;
- R$^3$ is a member selected from the group consisting of H, C$_1$–C$_8$ alkyl, CF$_3$ and O—R$^{12}$;
- R$^4$ is a member selected from the group consisting of H, C$_1$–C$_8$ alkyl, CF$_3$ and O—R$^{13}$;
- R$^5$ is a member selected from the group consisting of H, C$_1$–C$_8$ alkyl, CF$_3$ and O—R$^{14}$;
- R$^6$ is a member selected from the group consisting of H, C$_1$–C$_8$ alkyl, CF$_3$ and O—R$^{15}$;
- R$^7$ is a member selected from the group consisting of H, C$_1$–C$_8$ alkyl, CF$_3$ and O—R$^{16}$;
- R$^8$ is a member selected from the group consisting of H, C$_1$–C$_8$ alkyl, CF$_3$ and O—R$^{17}$;
- R$^9$ is a member selected from the group consisting of H, C$_1$–C$_8$ alkyl, CF$_3$ and O—R$^{18}$;
- R$^{10}$ is a member selected from the group consisting of H, C$_1$–C$_8$ alkyl, CF$_3$ and O—R$^{19}$;
- R$^{11}$ is a member selected from the group consisting of H, C$_1$–C$_8$ alkyl, CF$_3$ and O—R$^{20}$;
- R$^{12}$, R$^{13}$, R$^{14}$, R$^{15}$, R$^{16}$, R$^{17}$, R$^{18}$, R$^{19}$ and R$^{20}$ are each independently selected from the group consisting of C$_1$–C$_4$ alkyl, cycloalkyl and benzyl;

and all pharmaceutically acceptable stereoisomers, and prodrugs thereof.

2. The compound according to claim 1 wherein A is a member selected from the group consisting of:

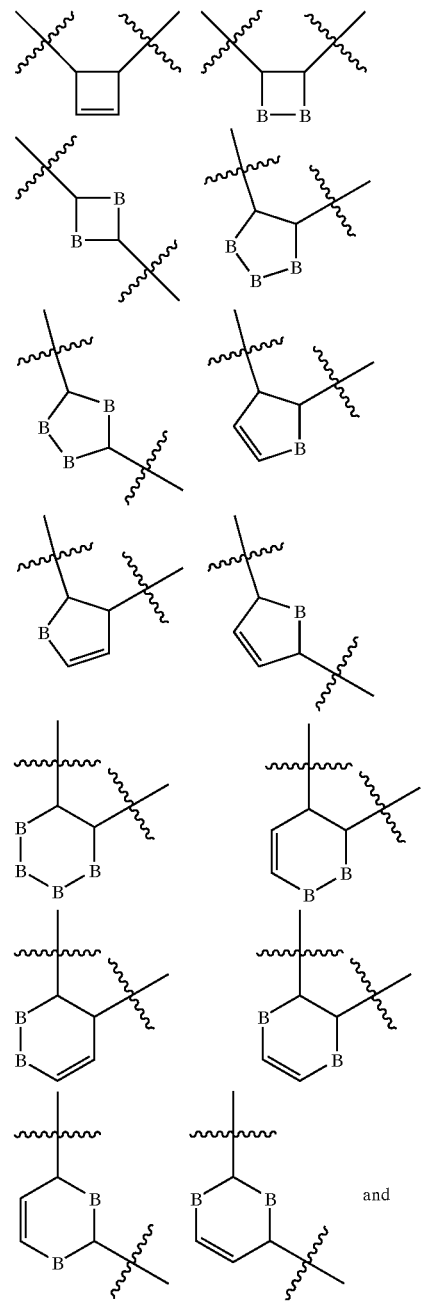

-continued

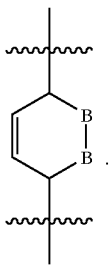

3. The compound according to claim 1 wherein A is a member selected from the group consisting of:

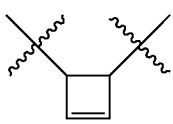
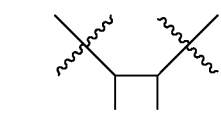

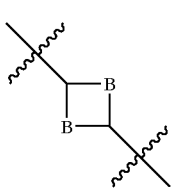
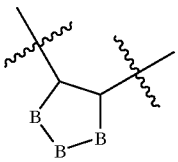

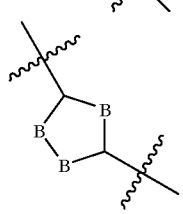

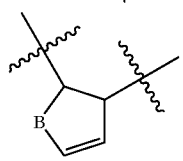
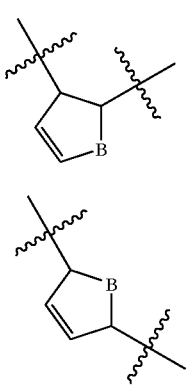

and

Y is a member selected from the group consisting of —(CH$_2$)$_q$— and —(CH$_2$)$_m$O—;

L is a member selected from the group consisting of —(CH$_2$)$_q$— and —(CH$_2$)$_m$O—; and R$^1$ is a member selected from the group consisting of H and —O—J$^5$—R$^8$; and R$^2$ is a member selected from the group consisting of H and —O—J$^8$—R$_{11}$;

and all pharmaceutically acceptable salts thereof.

4. The compound according to claim 1, wherein A is a member selected from the group consisting of:

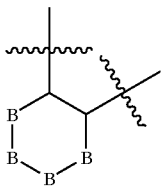
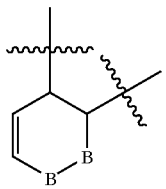

-continued

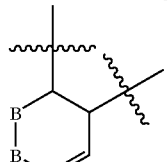
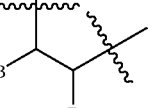

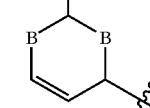
and

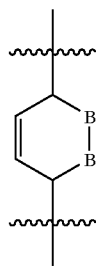

Y is a member selected from the group consisting of —(CH$_2$)$_q$— and —(CH$_2$)$_m$O—;

L is a member selected from the group consisting of —(CH$_2$)$_q$— and —(CH$_2$)$_m$O—; and R$^1$ is a member selected from the group consisting of H and —O—J$^5$—R$^8$; and R$^2$ is a member selected from the group consisting of H and —O—J$^8$—R$^{11}$;

and all pharmaceutically acceptable salts thereof.

5. A compound of the formula (I):

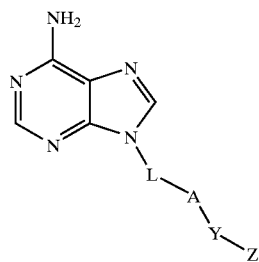

I wherein A is a member selected from the group consisting of:

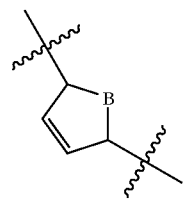
and
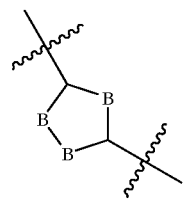

each B is CH$_2$;

Y is a member selected from the group consisting of —(CH$_2$)$_q$— and —(CH$_2$)$_m$O—;

Z is —(CH$_2$)$_n$—C(=O)—NHOH;

L is —(CH$_2$)$_q$—;

each m and n is independently an integer from 0 to 4; and each q is independently an integer from 0 to 8;

and all pharmaceutically acceptable salts thereof.

6. A pharmaceutical composition comprising an effective amount of a compound according to claim 1, or a pharmaceutically acceptable salt thereof, and a pharmaceutically acceptable diluent or carrier.

7. The pharmaceutical composition comprising an effective amount of a compound according to claim 2, or a pharmaceutically acceptable salt thereof, and a pharmaceutically acceptable diluent or carrier.

8. The pharmaceutical composition comprising an effective amount of a compound according to claim 3, or a pharmaceutically acceptable salt thereof, and a pharmaceutically acceptable diluent or carrier.

9. The pharmaceutical composition comprising an effective amount of a compound according to claim 4, or a pharmaceutically acceptable salt thereof, and a pharmaceutically acceptable diluent or carrier.

10. The pharmaceutical composition comprising an effective amount of a compound according to claim 5, or a pharmaceutically acceptable salt thereof, and a pharmaceutically acceptable diluent or carrier.

11. A method of treating congestive heart failure comprising administering an effective amount of a pharmaceutical composition according to claim 6 to a patient in need thereof.

12. A method of treating congestive heart failure comprising administering an effective amount of a pharmaceutical composition according to claim 7 to a patient in need thereof.

13. A method of treating congestive heart failure comprising administering an effective amount of a pharmaceutical composition according to claim 8 to a patient in need thereof.

14. A method of treating congestive heart failure comprising administering an effective amount of a pharmaceutical composition according to claim 9 to a patient in need thereof.

15. A method of treating congestive heart failure comprising administering an effective amount of a pharmaceutical composition according to claim 10 to a patient in need thereof.

* * * * *